United States Patent
Lawing et al.

(10) Patent No.: US 10,471,411 B2
(45) Date of Patent: Nov. 12, 2019

(54) POROUS MEDIA COMPOSITIONS AND METHODS FOR PRODUCING THE SAME

(71) Applicant: Advanced Materials Technology, Wilmington, DE (US)

(72) Inventors: Andrew Scott Lawing, Newark, DE (US); Timothy J. Langlois, Wilmington, DE (US); Daniel Brian Messick, Jr., Wilmington, DE (US); Brian M. Wagner, Cochranville, PA (US)

(73) Assignee: Advanced Materials Technology, Wilmington, DE (US)

( * ) Notice: Subject to any disclaimer, the term of this patent is extended or adjusted under 35 U.S.C. 154(b) by 694 days.

(21) Appl. No.: 14/790,997

(22) Filed: Jul. 2, 2015

(65) Prior Publication Data
US 2016/0030923 A1    Feb. 4, 2016

Related U.S. Application Data

(60) Provisional application No. 62/020,433, filed on Jul. 3, 2014.

(51) Int. Cl.
  *B01D 15/08*  (2006.01)
  *B01D 39/16*  (2006.01)
  (Continued)

(52) U.S. Cl.
  CPC .......... *B01J 20/3078* (2013.01); *B01D 15/08* (2013.01); *B01D 39/1661* (2013.01); *B01J 20/06* (2013.01);
  (Continued)

(58) Field of Classification Search
  CPC ...... B01D 15/08; B01D 39/1661; B01J 20/06; B01J 20/08; B01J 20/103; B01J 20/28004;
  (Continued)

(56) References Cited

U.S. PATENT DOCUMENTS

| | | | |
|---|---|---|---|
| 3,991,029 A * | 11/1976 | Adelman | .............. C04B 35/634 523/410 |
| 4,775,520 A | 10/1988 | Unger et al. | |

(Continued)

OTHER PUBLICATIONS

Liu et al., "Processing and characterizations of 2%PF/silica sand core-shell composite powders by selective laser sintering with a higher transmittance fiber laser," International Journal of Machine Tools & Manufacture 60 (2012), 52-58. (Year: 2012).*

(Continued)

*Primary Examiner* — Lucas A Stelling
(74) *Attorney, Agent, or Firm* — Riverside Law LLP

(57) ABSTRACT

The present invention relates to porous substrate compositions and methods for producing such compositions. In one embodiment, the porous substrate composition of the present invention comprises sintered spherical particles of a substantially uniform size. The porous media compositions of the present invention comprise relatively randomly-ordered particles with a void fraction significantly higher than compositions with a more ordered, close-packed configuration. The present invention further relates to composite porous media compositions comprising two or more relatively discrete layers of sintered particles.

24 Claims, 16 Drawing Sheets

(51) Int. Cl.

| | | |
|---|---|---|
| *B01J 20/06* | (2006.01) | |
| *B01J 20/08* | (2006.01) | |
| *B01J 20/10* | (2006.01) | |
| *B01J 20/28* | (2006.01) | |
| *B01J 20/283* | (2006.01) | |
| *B01J 20/30* | (2006.01) | |
| *B01J 20/32* | (2006.01) | |
| *B01J 20/281* | (2006.01) | |
| *G01N 30/60* | (2006.01) | |
| *G01N 30/52* | (2006.01) | |

(52) U.S. Cl.
CPC .............. *B01J 20/08* (2013.01); *B01J 20/103* (2013.01); *B01J 20/283* (2013.01); *B01J 20/28004* (2013.01); *B01J 20/28019* (2013.01); *B01J 20/28042* (2013.01); *B01J 20/3007* (2013.01); *B01J 20/3042* (2013.01); *B01J 20/3085* (2013.01); *B01J 20/3204* (2013.01); *B01J 20/3236* (2013.01); *B01J 20/3289* (2013.01); *B01J 20/3293* (2013.01); *B01J 20/3295* (2013.01); *G01N 30/482* (2013.01); *G01N 30/603* (2013.01); *G01N 2030/528* (2013.01)

(58) Field of Classification Search
CPC ............ B01J 20/28019; B01J 20/28042; B01J 20/283; B01J 20/3007; B01J 20/3042; B01J 20/3078; B01J 20/3085; B01J 20/3204; B01J 20/3236; B01J 20/3289; B01J 20/3293; B01J 20/3295; G01N 30/482; G01N 30/603; G01N 2030/528
See application file for complete search history.

(56) References Cited

U.S. PATENT DOCUMENTS

| | | |
|---|---|---|
| 4,826,727 A | 5/1989 | Glaser |
| 5,846,664 A | 12/1998 | Third et al. |
| 7,041,623 B2 | 5/2006 | Kirkland et al. |
| 7,717,271 B2 | 5/2010 | Ramaswamy et al. |
| 7,846,337 B2 | 12/2010 | Chen et al. |
| 8,561,271 B2 | 10/2013 | Chai |
| 8,702,946 B1 | 4/2014 | Chirica et al. |
| 9,263,166 B2 | 2/2016 | Handwerker |
| 2003/0118481 A1* | 6/2003 | Briscoe ............... F04B 19/006 422/89 |
| 2006/0167147 A1* | 7/2006 | Asgari ............... B01J 13/0091 524/174 |
| 2007/0189944 A1 | 8/2007 | Kirkland et al. |
| 2009/0297853 A1 | 12/2009 | Kirkland et al. |
| 2010/0029810 A1 | 2/2010 | Pantke et al. |
| 2010/0206797 A1* | 8/2010 | Chen ............... B01J 20/28004 210/263 |
| 2011/0310528 A1 | 12/2011 | Chai |
| 2012/0262836 A1 | 10/2012 | Chai |
| 2014/0370322 A1 | 12/2014 | Handwerker |

OTHER PUBLICATIONS

Stöber, et al., "Controlled Growth of Monodisperse Silica Spheres in the Micron Size Range," Journal of Colloid and Interface Science. 1968. 26:62-69.

Rahaman, 2003, Ceramic Processing and Sintering, $2^{nd}$ edition, CRC press, pp. 1-876.

Snyder et al. Introduction to Modern Liquid Chromatography, $3^{rd}$ Edition, Wiley, 2010, pp. C1-912.

* cited by examiner

POROUS MEDIA COMPOSITIONS AND METHODS FOR PRODUCING THE SAME

CROSS-REFERENCE TO RELATED APPLICATIONS

This application claims priority to U.S. Patent Application Ser. No. 62/020,433, filed Jul. 3, 2014, the entire contents of which are incorporated herein by reference.

BACKGROUND OF THE INVENTION

Porous media are used for a variety of applications, such as filtration and chromatography. In such applications, it is desirable for the porous media to exhibit maximum solids retention characteristics while also allowing a high rate of fluid throughput. Porous media fabricated from a plurality of spherical particles can provide excellent retention characteristics due to the spatially uniform packing characteristics of spheres. However, fabricating media from spherical particles typically results in a close-packed particle configuration, i.e., a configuration with a void fraction at or close to the theoretical minimum void fraction. Such a configuration maximizes retention characteristics, but also minimizes the interstitial space between the particles, thereby resulting in a media with undesirable fluid throughput. In other words, the packing of the spheres increases the solids retention, but also decreases the maximum flow rate of fluids through the media due to the minimal void fraction.

Thus, there is a need in the art for a porous media with excellent solids retention characteristics, but with a relatively high void fraction to allow for high fluid throughput. The present invention addresses this unmet need in the art.

SUMMARY OF INVENTION

The present invention relates to porous media compositions and methods for producing such compositions. In one embodiment, the composition of the present invention is a sintered porous material, comprising: one or more layers of sintered silica particles having a void fraction of at least about 0.26, wherein each layer comprises substantially spherical particles having a relative standard deviation in particle size of about 10% or less. In various embodiments, the average particle size of the particles can be greater than about 1 micron; about 1.7 micron; or greater than about 3 micron. In various embodiments, the average particle size of the particles can be less than about 1 micron; less than about 500 nm; less than about 250 nm; or less than about 50 nm.

In another embodiment, the material of the present invention is a sintered porous material, comprising: a substrate layer of sintered silica particles having a void fraction of at least about 0.26, wherein the substrate layer comprises substantially spherical particles having a relative standard deviation in particle size of about 10% or less, and a second layer of sintered silica particles, wherein the second layer comprises substantially spherical particles having a relative standard deviation in particle size of about 10% or less, wherein the diameter of the second layer particles is about 50 percent or less than the diameter of the substrate layer particles, and wherein the second layer is sintered to the substrate layer. In such an embodiment, the material can further comprise one or more additional layers of sintered silica particles, wherein the one or more additional layers comprises substantially spherical particles having a relative standard deviation in particle size of about 10% or less, wherein the diameter of the particles in each additional layer is about 50 percent or less than the diameter of the particles in the previous layer, and wherein each additional layer is sintered to the previous layer. In various embodiments, the average particle size of the particles in the substrate layer can be greater than about 1 micron; about 1.7 micron; or greater than about 3 micron. In various embodiments, the average particle size of the particles in the substrate layer can be less than about 1 micron; less than about 500 nm; less than about 250 nm; or less than about 50 nm.

In one embodiment, the silica particles of the material of the present invention can comprise a substantially solid silica core, and one or more shell layers, wherein each shell layer comprises a plurality of sintered silica shell particles. In one embodiment, the one or more shell layers are less porous than the silica core. In another embodiment, the one or more shell layers are more porous than the silica core.

In one embodiment, the material of the present invention has a void fraction of at least 0.4. In another embodiment, the material of the present invention has a void fraction of at least 0.5.

In one embodiment, the method of the present invention is a method of making a sintered porous material comprising: dispersing a plurality of substantially spherical silica core particles in a mixture comprising a polymer and a liquid, removing at least a portion of the liquid, and sintering the silica particles to form a sintered porous material having a void fraction greater than about 0.26.

In another embodiment, the method of the present invention is a method of making a sintered porous material comprising: providing a plurality of substantially spherical silica core particles, contacting the silica particles with an acid to hydroxylate at least a portion of the surface of the silica particles, removing at least a portion of the acid, contacting the silica particles with a polymer such that at least a portion of the surface of the silica particles is coated with the polymer, drying the polymer-coated silica particles, and sintering the silica particles to form a sintered porous material.

In yet another embodiment, the method of the present invention is a method of making a sintered porous material comprising: providing a plurality of substantially spherical silica core particles, contacting the silica particles with an acid to hydroxylate at least a portion of the surface of the silica particles, removing at least a portion of the acid, contacting the silica particles with a polymer such that at least a portion of the surface of the silica particles is coated with the polymer, forming a plurality of core-shell silica particles by contacting the polymer-coated silica core particles with a plurality of shell silica particles, wherein the plurality of shell silica particles are bound to the polymer coated silica core particles, drying the core-shell silica particles, and sintering the core-shell silica particles to form a sintered porous material. In such an embodiment, the method can further comprise one or more additional shell-forming steps, wherein each shell forming step comprises: contacting the core-shell silica particles with a polymer such that at least a portion of the surface of the core-shell silica particles is coated with polymer, and contacting the polymer-coated silica core-shell particles with a plurality of shell silica particles, wherein the plurality of shell silica particles are bound to the polymer coated core-shell silica particles.

In one embodiment, the methods of the present invention can further comprise the steps of suspending the dried silica particles in a binding solution to form a binding mixture, and extruding the binding mixture to form a tape comprising silica particles prior to sintering. In such an embodiment, two or more tapes comprising silica particles can be stacked prior to sintering. In such an embodiment, the method can further comprise applying at least one adhesive layer between the two or more tapes. In such an embodiment, the adhesive layer comprises sol silica particles. In another such embodiment, the adhesive layer comprises a slurry comprising the tape material and a solvent. In one embodiment, the binding solution comprises a binder. In such an embodiment, the binder can be selected from the group consisting of: poly(styrene sulfonic acid), poly(ethylene oxide), poly vinyl acetate-acrylic co-polymer, poly(vinyl alcohol), polyvinylpyrrolidone, poly(acrylic acid), poly(methylacrylic acid), polyacrylamide, polyethylenimine, methylcellulose, hydroxypropylmethylcellulose, hydroxyethylcellulose, sodium carboxymethylcellulose, poly(vinyl butyral), poly (vinyl formal), poly(methyl methacrylate), a starch, a dextrin, and an alginate. In one embodiment, the binding solution comprises a plasticizer. In such an embodiment, the plasticizer can be selected from the group consisting of: poly(ethylene glycol), ethylene glycol, diethylene glycol, triethylene glycol, tetraethylene glycol, poly(alkylene glycol), a glycerol, and a phthalate. In one embodiment, the binding solution comprises a polymer. In such an embodiment, the polymer can be selected from the group consisting of poly(diallyldimethylammonium) chloride (PDDA), poly (diethylaminoethylmethacrylate) acetate (poly-DEAM), poly-p-methacrylyloxyethyldiethylmethyl ammonium methyl sulfate (poly-p-MEMAMS), and polymethacrylic acid.

In one embodiment of the method of the present invention, the average particle size of the silica core particles can be less than about 1 micron; greater than about 1 micron; about 1.7 micron; or greater than about 3 micron. In one embodiment of the method of the present invention, the average particle size of the shell silica particles can be about 9 nm. In one embodiment of the method of the present invention, the void fraction of the sintered porous material is greater than about 0.4. In one embodiment of the method of the present invention, the void fraction of the sintered porous material is greater than about 0.5.

The present invention also relates to implements made of the sintered porous material described herein, methods for making such implements, and devices incorporating such implements. In one embodiment, the methods described herein can further comprise forming a sintered porous implement from the sintered porous material and sealing an edge of the implement. In one embodiment, the implement is formed by cutting the sintered porous material with a laser. In one embodiment, the implement is a frit for a chromatography column, comprising the sintered porous material. In one embodiment, the frit is cut from a sheet or plate of sintered porous material using a laser. In one such embodiment, the laser cutting substantially seals the edges of the frit. In another embodiment, the frit can be cut from a sheet or plate using any suitable technique other than a laser. In another such embodiment, the present invention relates to a packing material for a chromatographic device or column, comprising the sintered porous material. In another such embodiment, the present invention relates to a filter comprising the sintered porous material. In yet another such embodiment, the present invention relates to a solid phase extraction device, having an extraction medium comprising the sintered porous material.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 13A is a high magnification electron micrograph of an exemplary embodiment of the porous media of the present invention fabricated by tape casting. FIG. 13B is a low magnification electron micrograph of an exemplary embodiment of the porous media of the present invention fabricated by tape casting.

DETAILED DESCRIPTION

Figure 1A:
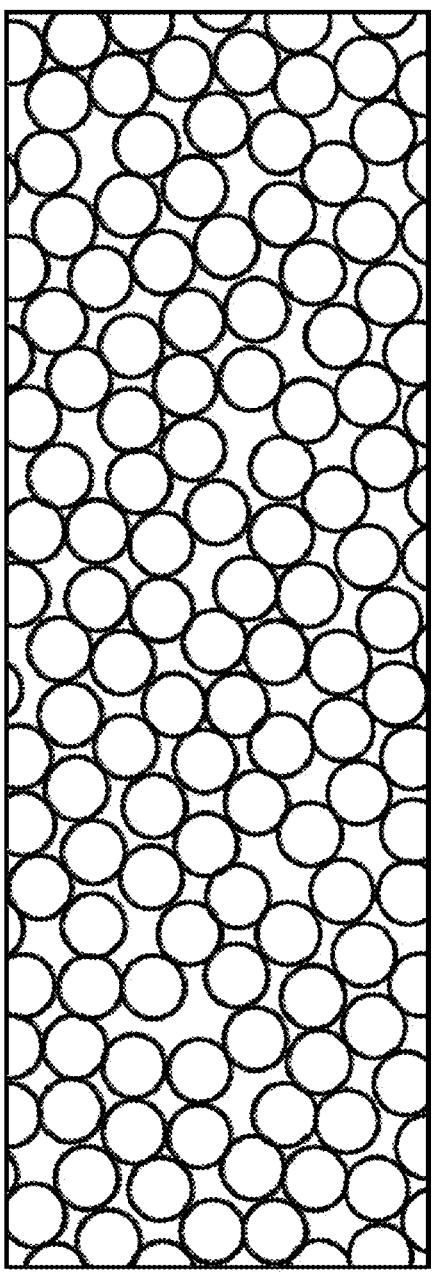
FIGS. 1A and 1B are a set of schematic diagrams showing a loose random packing of spheres (FIG. 1A) and a closest packed configuration of spheres (FIG. 1B).

It is to be understood that the figures and descriptions of the present invention have been simplified to illustrate elements that are relevant for a clear understanding of the present invention, while eliminating, for the purpose of clarity, many other elements found in the art related to porous media and methods of making porous media, including tape casting and the like. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The terms "green," "green state," "green part," "green layer," and the like, are used interchangeably herein, and refer to unsintered particles or unsintered particle layers, i.e., particles suitable for sintering, but prior to being sintered.

The term "layer" when used herein in reference to the sintered porous media of the present invention refers to a plurality of particles that have been sintered together to form the porous media. The thickness of any single "layer" can be a single particle thick or it can be significantly more thick than a single particle, for example, but not limited to, tens, hundreds, thousands, or millions of particles in thickness. Accordingly, the use of the term "layer" is meant to refer to any grouping of sintered porous particles of substantially similar shape and size.

The term "frit," as it is used in this disclosure, refers to a device that can be used on the inlet and/or outlet end of a chromatographic column. The function of a frit is to retain any particles, e.g., packing media particles, contained in the column, as well as to evenly distribute an injected sample across most or all of the cross section of the column diameter as the sample is introduced into the column.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

The present invention relates to porous media compositions and methods for producing such compositions. In one embodiment, the porous media composition of the present invention comprises sintered particles of a substantially uniform shape and size. In one embodiment, the particles are substantially spherical in shape. In one embodiment, the particles comprise silica. The porous media compositions of the present invention comprise relatively randomly-ordered particles with a void fraction significantly higher than compositions with a more ordered, close-packed configuration. The present invention further relates to composite porous media compositions comprising two or more relatively discrete layers of sintered particles that are sintered to each other.

The porous compositions of the present invention have utility in a broad range of applications, including physical separations, such as filtration; chemical separations, such as chromatography; and sample preparation, such as solid phase extraction. The methods of making the compositions of the present invention can be used to produce porous media with well-controlled pore size distribution and solids-retention characteristics. Further, the retention characteristics of the porous media can be modified according to the needs of the respective application.

Compositions

Figure 1B:
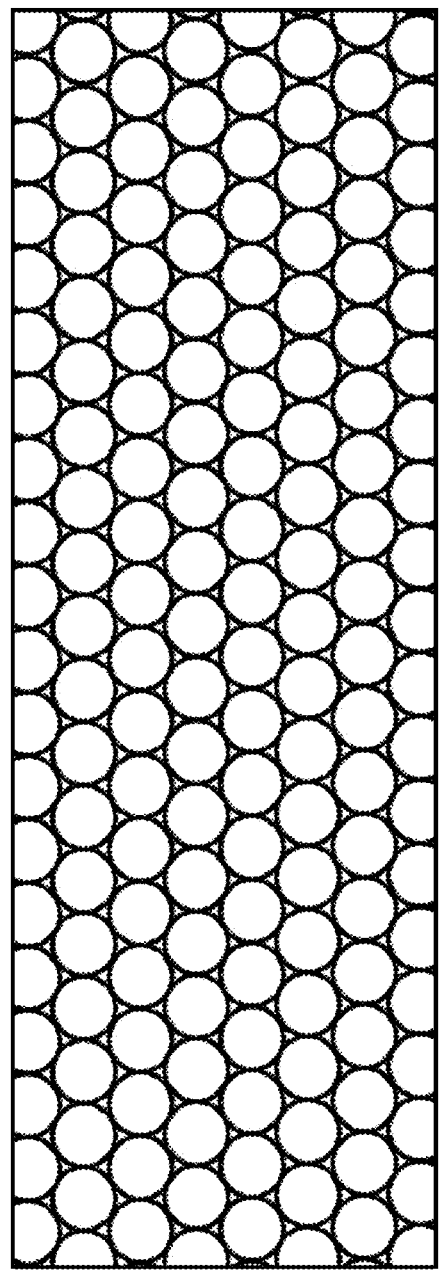

In various embodiments, the porous media of the present invention comprise substantially spherical particles in a loosely-packed configuration, i.e., the media have a relatively high void fraction. Referring now to FIG. 1, an illustration showing examples of the configuration of the packing of spheres in a porous media is shown. FIG. 1A shows the random, loose packing of spheres, while FIG. 1B shows a close-packed configuration. The compositions of the present invention exhibit relatively loose packing of particles, i.e., packing similar to that shown in FIG. 1A, which results in these compositions having both desirable retention and fluid flow characteristics.

Figure 2B:
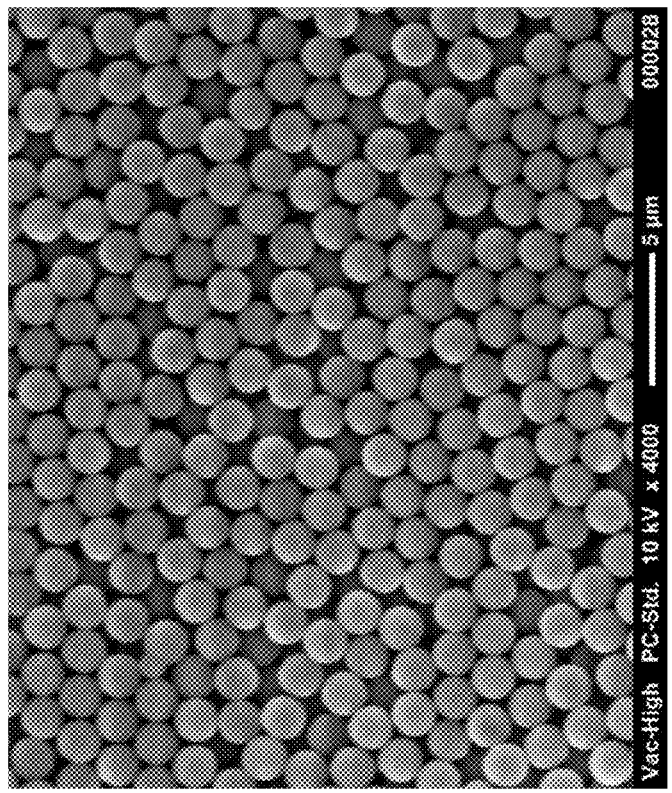
FIGS. 2A and 2B are a set of scanning electron micrographs showing a synthetic opal structure, illustrating a closest packed configuration of spheres (FIG. 2A) and silica spheres deposited by a filtration technique, illustrating a loose random packing of spheres (FIG. 2B).
Figure 2A:
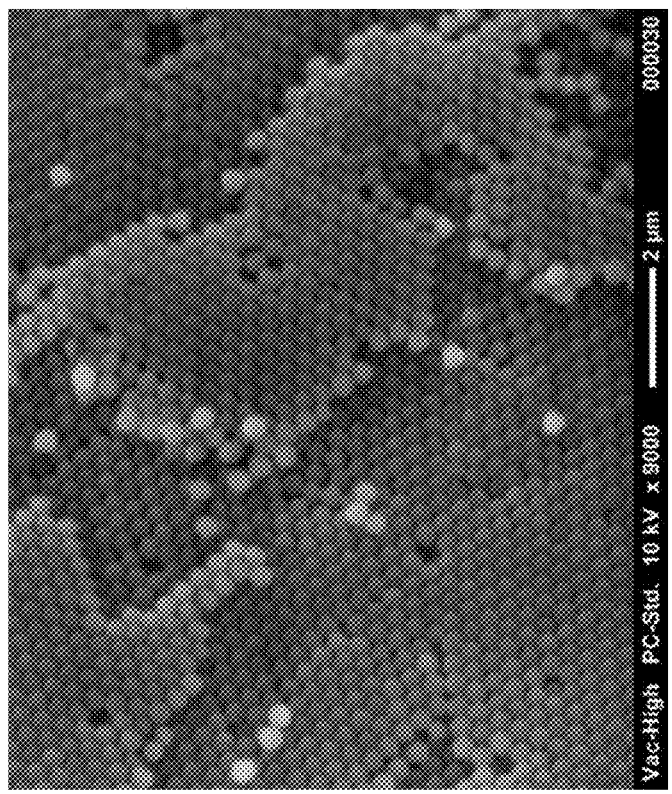

Referring now to FIG. 2, Scanning Electron Micrographs (SEM) for both close (FIG. 2A) and loose (FIG. 2B) packed silica particles are shown. In FIG. 2A, arrays of silica spheres tend to self-align into closest-packed structures when deposited by sedimentation or centrifugation techniques, especially under favorable dispersion conditions, thereby forming a synthetic opal. The material in FIG. 2A has "opalescent" bulk optical properties, indicating significant long-range order in the structure. In comparison, the structure shown in FIG. 2B has a more random, loose-packed structure, although some localized, short-range order is present. In general, porous media exhibiting structures other than the closest-packed configuration provide a number of advantages, such as allowing higher fluid flow rates than close-packed substrates while providing similar retention characteristics.

The porous substrate compositions of the present invention have a void fraction that is greater than the void fraction of a theoretical closest-packed configuration of same-sized spheres, i.e., a porous media having a relatively loose-packed structure. Accordingly, in various embodiments, the porous media of the present invention have a void fraction significantly greater than 0.26. In one embodiment, the void fraction of the substrate is greater than the typical loose random packing of spheres. In another embodiment, the void fraction of the substrate is greater than the thinnest regular packing of same-sized spheres. In yet another embodiment, the void fraction of the substrate is greater than about 0.4, but with a population of randomly distributed and localized close-packed events. In one such embodiment, the close-packed events can be limited to, on average, three adjacent particles.

In addition, the compositions of the present invention can comprise a composite material having two or more layers of particles. Each layer can comprise sintered particles that are substantially uniform in size and shape within the layer. Further, the adjacent layers can be sintered to each other to form the composite material. In one embodiment, each sequential layer in the composite material can comprise particles that, on average, are significantly different in size than the previous layer. For example, in one embodiment, the average particle size of each sequential layer can be smaller or larger by a factor of two compared to an adjacent layer. In some embodiments, the diameter of the particles in each layer become progressively smaller compared to the previous layer. In one embodiment, the one or more layers of the composite material can be relatively discrete, such that distinct layers can be observed when viewing a cross-section of the composite material. In another embodiment, the one or more layers of the composite material can be relatively indiscrete, such that distinct layers cannot be readily observed when viewing a cross-section of the composite material.

In one embodiment, one or more of the layers can have a void fraction significantly greater than the theoretical density for a closest-packed configuration of spheres. In another embodiment, one or more of the layers can have a void fraction greater than a typical loose random packing of spheres. In yet another embodiment, one or more of the layers can have a void fraction that is greater than the thinnest regular packing of spheres. In some embodiments, each of the plurality of layers has a void fraction that is significantly greater than the theoretical void fraction for a closest-packed configuration of spheres; each of the plurality of layers has a void fraction that is greater than the typical loose random packing of spheres; or each of the plurality of layers has a void fraction that is greater than the thinnest regular packing of spheres.

The substantially spherical particles in the compositions of the present invention can comprise a variety of different materials. In a preferred embodiment, the particles can comprise silica. In other embodiments, the particles can comprise any other material suitable for forming substantially spherical particles as would be understood by a person skilled in the art, such as, but not limited to: a metal oxide, such as titania, alumina, antimony oxide, zinc oxide, tin oxide or iron oxide, an inorganic oxide, any type of stainless steel or steel alloy, titanium or any other metal, or a polymer or plastic.

In one embodiment, the particles can comprise a core-shell particle. A core-shell particle comprises a solid core, for example a core made of silica, and one or more shell layers. In one embodiment, the one or more shell layers can comprise a polymer. In another embodiment, the one or more shell layers comprise a mixture of a polymer and sol particles, i.e., particles significantly smaller in size than the core. For example, in one such embodiment, the core-shell particle can comprise a substantially solid silica core that is coated with one or more shell layers comprising small silica particles embedded in a polymer. In yet another embodiment, the one or more shell layers are composed of primarily only sol particles. In one such embodiment, the sol particles can form a shell around the core particle that is less dense than the core particle, i.e., the shell layer can have a higher porosity than the core. In various embodiments, the shell of the core-shell particle can be sintered at a lower temperature than the core. In such embodiments, this is primarily due to the smaller particle size, and therefore higher relative surface area, of the shell portion compared to the core portion. Accordingly, the shells of adjacent particles can be sintered together without affecting the morphology or integrity of the core portion of the core-shell particles. In one embodiment, the shell or sol particles can be composed of a different material than the core. For example, in one such embodiment, the porous media of the present invention can comprise particles having an iron oxide core and a shell comprising silica.

In various embodiments, the substantially spherical particles in the composition of the present invention can be any size, as would be understood by a person skilled in the art. In one embodiment, the particles can be in the range of about 9 nanometer (nm) to 10 micron, or larger, for example, but not limited to 20 nm, 50 nm, 100 nm, 0.5 micron, 1 micron, 1.7 micron, 3 micron, or 5 micron. In one embodiment, the core portion of the core-shell particle is in the range of 9 nm to 10 micron or larger. Further, the sol particles used in the shell of the core-shell particles can be any size, as would be understood by a person skilled in the art. In one embodiment, the sol particles can be in the range of about 1 nm to 1 micron, for example, but not limited to 2 nm, 5 nm, 7 nm, 9 nm, 50 nm, or 100 nm. However, the sol particles can be any particle size that is significantly smaller than the core particles it is associated with. The sol particles can form a shell around a core portion that is in the range of a few nanometers up to about 1 micron. In one embodiment, the size of the sol shell is about 0.5 micron. In various embodiments, the sol shell is about one order of magnitude smaller than the core portion.

In a preferred embodiment, the substantially spherical particles in the composition of the present invention, or within a single layer of the composite compositions of the present invention, are substantially same-sized. Accordingly, in one embodiment, the substantially spherical particles have a relative standard deviation in particle size of about 10% or less. In other embodiments, the substantially spherical particles have a relative standard deviation in particle size other than 10% or less, for example, but not limited to: 1% or less, 5% or less, 20% or less, 30% or less, or 50% or less.

The compositions of the present invention can also comprise additional materials that can be used to optimize various characteristics of the compositions. For example, in some embodiments, the compositions can include binders, plasticizers, or other additives that can be used to bind the particles of the composition together or to hold the particles in a desired packing position prior to sintering the particles. In one embodiment, the binders, plasticizers, or other additives are substantially or completely removed during sintering, for example as a result of degradation due to the heat of the sintering process. In another embodiment, a portion of the binders, plasticizers, or other additives can remain after the sintering or other processing steps are performed to create the sintered porous material of the present invention.

In some embodiments, at least a portion of the porous media can be functionalized with various functional groups or otherwise chemically treated to change the retention characteristics of the media. As would be understood by a person skilled in the art, functionalization or chemical modification of the porous media can be useful for some applications, such as chromatography. For example, the porous media can be functionalized to have a negative or positive charge, or to otherwise increase or decrease the affinity of the media to a specific type of molecule. In one embodiment, the particles of the porous media can be functionalized. In another embodiment, the particles can be coated with a material, such as a polymer as described above, to change the affinity characteristics of the porous media. In yet another embodiment, the shell or coating of the particles can be functionalized, for example, after the sintering process has been completed. In one such embodiment, the surface of the particles can be functionalized with an octadecyl carbon chain ($C_{18}$), an octyl carbon chain ($C_8$), a phenyl group, or a cyano group.

Void Fraction and Retention Characteristics

As described herein, the compositions of the present invention comprise porous media with relatively high void fractions, i.e., void fractions of about 0.4 or greater. Table 1 provides some examples of the void fraction and packing density associated with various sphere packing configurations. The configuration with the closet packing possible is the Hexagonally Closest Packed (HCP) configuration, with a void fraction of about 0.26. Random packing configurations can exhibit void fractions approaching 0.5.

TABLE 1

Void fraction and packing density of various sphere packing configurations.*

| Model | Description | Void fraction | Packing density |
|---|---|---|---|
| Thinnest regular packing | Coordination number = 6 | 0.4764 | 0.5236 |
| Very loose random packing | E.g., spheres slowly settling | 0.44 | 0.56 |
| Loose random packing | E.g., spheres dropped in- to bed or packed by hand | 0.40 to 0.41 | 0.59 to 0.60 |
| Poured random packing | Spheres poured into bed | 0.375 to 0.391 | 0.609 to 0.625 |
| Close random packing | E.g., the bed vibrated | 0.359 to 0.375 | 0.625 to 0.641 |
| Thickest regular packing | Coordination number = 12 | 0.2595 | 0.7405 |

*F. A. L. Dullien, "Porous Media. Fluid Transport and Pore Structure", 2nd edition, Academic Press Inc., 1992.

Figure 3:
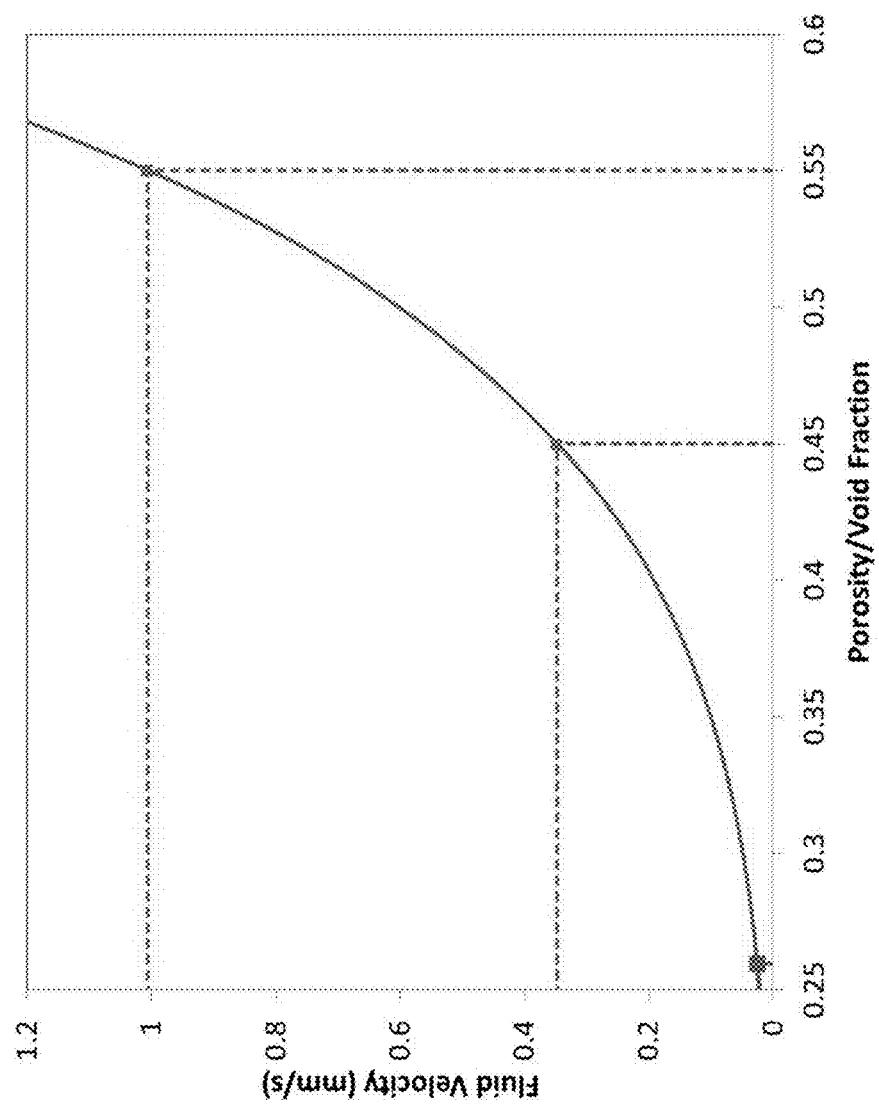
FIG. 3 is a graph showing the predicted fluid velocity as a function of void fraction for a 4 mm thick bed of 1.7 μm spheres at a pressure drop of 2 atm and a range of void fractions.

As contemplated herein, a porous material with a relatively high void fraction is desirable for use in filtration applications or other applications requiring the retention of solids while allowing fluids to pass through the pores. For example, the data illustrated in FIG. 3 show the efficacy of a loose-packed structure relative to the closest-packed structure. The fluid velocities in FIG. 3 were calculated based on Darcy's law:

$$V = \frac{K \delta P}{\mu \Delta x} \quad (1)$$

where v is equal to the fluid velocity, K is the permeability of the medium, ΔP is the pressure gradient across the porous medium, μ is the dynamic viscosity of the fluid and Δx is the thickness of the bed. For a bed of packed spheres, the permeability K, can be estimated as:

$$K = \frac{\varepsilon^3}{180(1-\varepsilon)^2} d^2 \quad (2)$$

according to the Carman-Kozeny model [Kaviany, 1991 "Principles of Heat Transfer in Porous Media", Springer-Verlag] or:

$$K = \frac{\varepsilon^{5.5}}{5.6} d^2 \quad (3)$$

according to Rumpf and Gupte [Rumpf and Gupte, 1975, "The influence of porosity and grain size distribution on the permeability equation of porous flow", Chemie Ing. Techn. (Weinheim), v. 43, no. 6, p 367-375], where ε is the porosity (or void fraction) of the bed and d is the diameter of the spherical particle. In FIG. 3, the permeability was calculated as the average of these two models to yield a predicted flow velocity for a given medium at a given pressure. Three hypothetical porous layers are represented in FIG. 3. All represent a 4 mm thick layer comprised of 1.7 μm particles at a pressure drop of 2 atm at void fractions of 0.26, 0.45, and 0.55, respectively. Predicted fluid velocity as a function of the void fraction of the bed is shown for the three hypothetical layers. As the void fraction is increased, the flow through the media increases dramatically. For example a void fraction of about 0.45 results in more than a tenfold increase in fluid velocity versus the HCP void fraction of 0.26 and the void fraction of 0.55 represents almost a 40 fold increase in fluid velocity versus the HCP void fraction.

Accordingly, a less dense packing of spheres, i.e., less than the closest theoretical packing, can provide an advantage for a porous media in terms of the volume of fluid that can be pushed through it at any given pressure drop. In addition, an absolute retention on the order of the retention of the HCP structure can still be obtained with the loose packed structure, provided that the bed is thick enough.

Referring again to FIG. 2, a material with an HCP structure is shown in FIG. 2A, while an example of one embodiment of a material of the present invention is shown in FIG. 2B. Although the structure of the material in FIG. 2B is substantially more open than that of the HCP structure shown in FIG. 2A, a packing similar to the HCP structure is still evident in a few relatively small, local regions. Therefore, even though the overall void fraction of the material in FIG. 2B is significantly higher than the HCP material, any statistical random path through the structure will encounter a blockage on the order of the space between closest packed spheres. Thus, the absolute solids retention of the material in FIG. 2B is defined by the interstitial space between the closest-packed particles, provided that the material is sufficiently thick. In the example shown in FIG. 3, a 4 mm layer of 1.7 μm spheres represents at least 2350 particle diameters. A 4 mm layer having a high void fraction, i.e., a void fraction of about 0.4 or greater, is sufficiently thick to exhibit an absolute retention substantially similar to the retention exhibited by an HCP structure. Thus, a porous bed comprised of a loose-packed structure of spherical particles can exhibit excellent retention, while also having significantly better flow characteristics than the HCP structure.

Figure 4B:
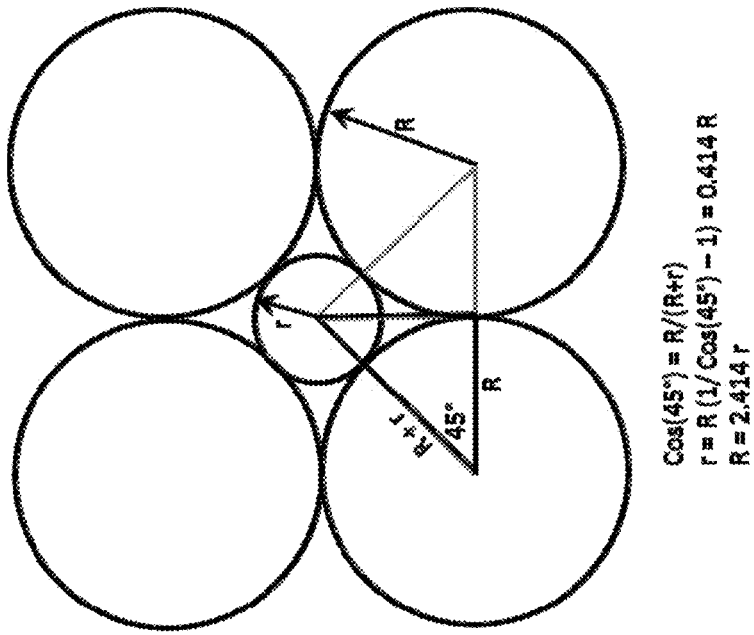
FIGS. 4A and 4B are a set of schematic diagrams showing the geometry of three spheres in a closest packed configuration, illustrating the size of the interstitial space (FIG. 4A) and the geometry of four spheres in a cubic configuration, illustrating the size of the interstitial space (FIG. 4B).
Figure 4A:
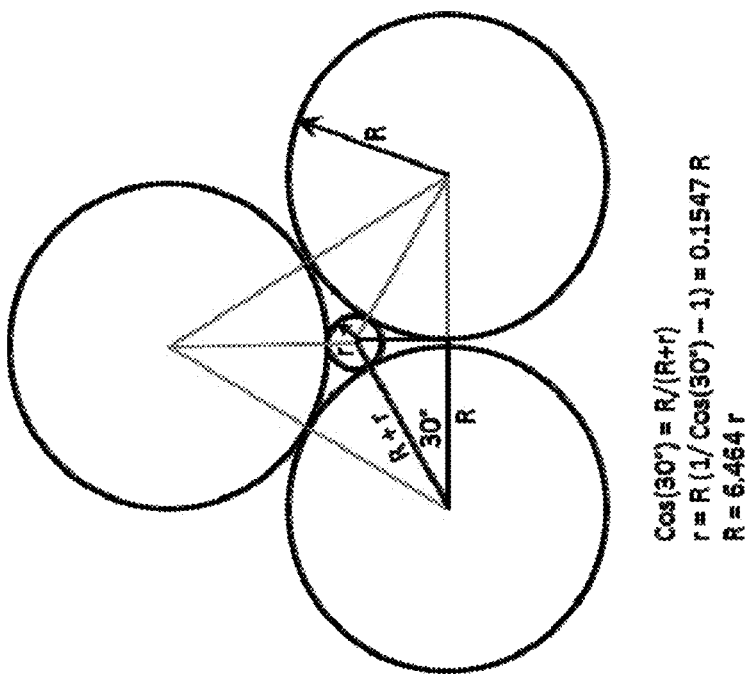

The interstitial space between packed spheres is important to consider for a number reasons. First, the interstices between nearest neighbors will define the retention characteristics of the media as discussed previously. Second, when fabricating a media comprised of sequential layers of spheres of differing size, the relative dimensions of the interstices of a first layer and the spheres comprising a second adjacent layer will determine to what extent the first and second layers will intermingle. FIG. 4 illustrates some basic geometrical considerations that define the extremes of nearest neighbor interstitial dimensions. FIG. 4A illustrates three spheres in an HCP configuration; with an interstitial space that would accommodate a secondary sphere of about 0.15 times the radius of the primary sphere, whereas the cubic configuration illustrated in FIG. 4B would accommodate a secondary sphere of about 0.4 times the radius of the primary sphere. Accordingly, the retention characteristics of the porous media compositions can depend on the interstitial space between particles within the same layer, or the interstitial spaces between particles from two adjacent layers.

Methods of Making Porous Media

The present invention also relates to methods of fabricating porous media and composite porous media. In various embodiments, the method of the present invention includes the steps of forming a layer of substantially spherical particles and then sintering the particles. In one embodiment, the layer can be formed via sedimentation or deposition from a dispersion comprising substantially spherical particles. In another embodiment, the layer can be formed via tape casting. In yet another embodiment, the layer can be formed via dip coating. In one embodiment, the method of the present invention is a method for fabricating a composite porous media having two or more connected layers of sintered particles. In one such an embodiment, a composite media can be fabricated by forming a first layer of particles, sintering the first layer, then forming a second layer of particles on the first layer and sintering the second layer. In one such embodiment, at least a portion of the particles at the interface between the first layer and the second layer are sintered together. Additional layers can then be added, if desired, by repeating the process. In another embodiment, a composite porous media can be fabricated by forming multiple unsintered, i.e., green-state, layers on top of each other and then sintering the multiple layers simultaneously.

In a preferred embodiment, the spherical particles are at least partially coated with polymer electrolyte, i.e., polyelectrolyte, prior to, or during, the layer forming process. The presence of the polymer electrolyte serves to increase the spacing between the particles during the layer-forming process, for example via electrostatic forces or steric hindrance. Accordingly, this increased spacing between the particles results in relatively high void fractions after sintering. Further, the conditions of the layer forming and/or sintering steps can be varied to control the void fraction of the resulting porous media. In one embodiment, the uncoated spherical particles may need to be pre-treated prior to coating with the polyelectrolyte in order to improve the binding of the polyelectrolyte to the particle. For example, in one embodiment, a silica particle can be hydroxylated via treatment with an acid, prior to being contacted with a polyelectrolyte, such as poly(diallyldimethylammonium) chloride (PDDA).

Figure 8:
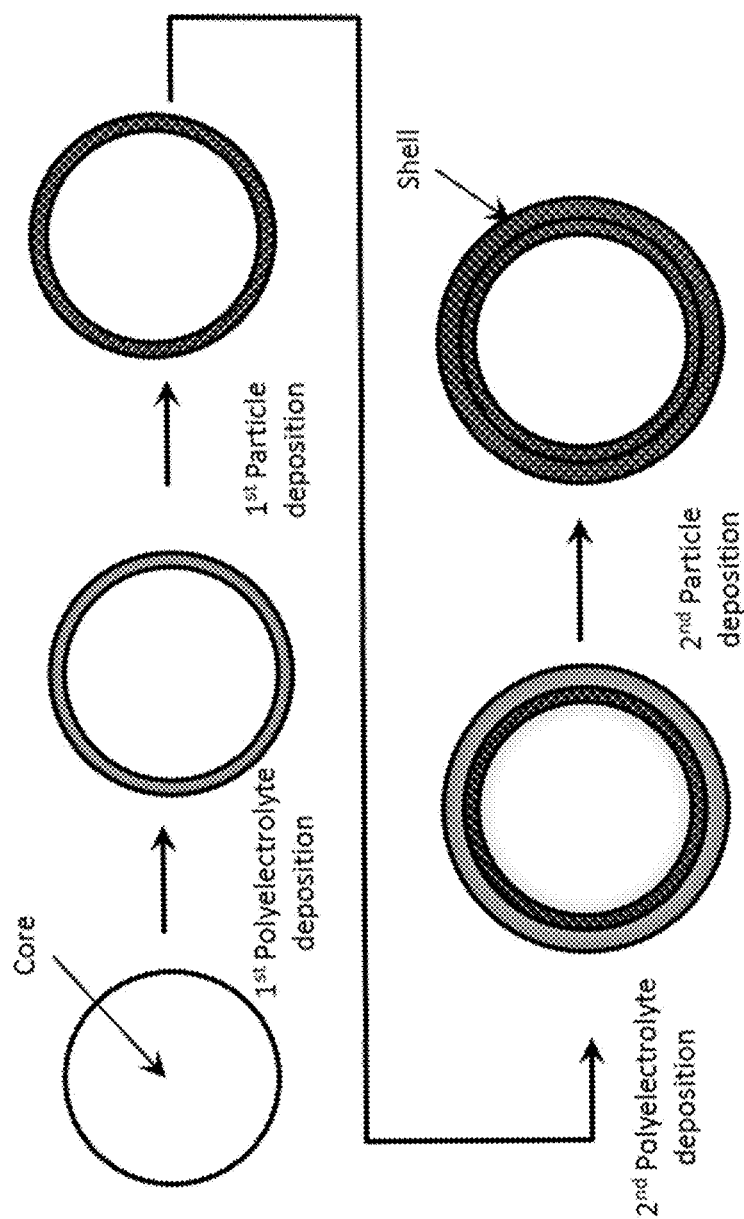
FIG. 8 is a schematic illustration of the shell formation process.

The method of the present invention can also include steps for forming the substantially spherical particles prior to fabricating the porous media. In various embodiments, the particles used in the method of the present invention can be formed via any processes known in the art for forming substantially spherical particles. In one embodiment, the particles used in the method are core-shell particles. In such an embodiment, core particles are first coated with a polyelectrolyte. The polymer-coated core particles are then contacted with a solution comprising shell particles, i.e., particles of significantly smaller size than the core particles. The smaller shell particles then become entangled in the polymer coating of the larger particles and form a shell around the larger particle. As shown in FIG. 8, this polyelectrolyte/particle coating process can be repeated multiple times to form a thicker, or multi-layered, shell around the core particle. An example of a core-shell particle forming process is described by Kirkland et al. (U.S. Pat. App. Pub. No. 2007/0189944, which is hereby incorporated by reference in its entirety). In other embodiments, core-shell particles can be formed via any manufacturing process known in the art, and the method of making core-shell particles for use in the sintered porous media of the present invention is not limited to the methods described by Kirkland et al. or any other method described herein. Chen et al. describe methods of forming cores shell particles comprised of silica and numerous other metal oxides (U.S. Pat. No. 7,846,337, which is hereby incorporated by reference in its entirety).

The resulting core-shell particle can then be used in a layer-forming step. In one embodiment, the shell of the core-shell particles can be at least partially consolidated prior to being used in a layer-forming step. In such an embodiment, the shell or sol particles in the shell are at least partially sintered to form a layer around the core that is more porous, i.e., less dense, than the core. In one embodiment, such consolidated core-shell particles remain discrete particles that are not sintered to each other prior to being used in a layer-forming step.

In one embodiment, a dispersion comprising the core-shell particles and a polymer electrolyte or binder system can be filtered in order to remove the excess liquid, for example after treating the particles with the polyelectrolyte. In one embodiment, this filtration step can be used to form a green layer, i.e., as the layer-forming step of the method of the present invention. In another embodiment, the particles can be dried after filtering and stored in the form of a powder comprising dry polyelectrolyte-coated particles or shell-core particles. In one such embodiment, the shell-core particles in the powder can have a shell that is at least partially consolidated, as previously described. Powders comprising dry polyelectrolyte-coated particles or core-shell particles can be utilized in tape casting or other deposition processes to form green layers or precursors. Polyelectrolyte-coated particles or core-shell particles can be dispersed in a wide variety of media including aqueous and non-aqueous dispersions comprising polymer binders and plasticizers.

Figure 5:
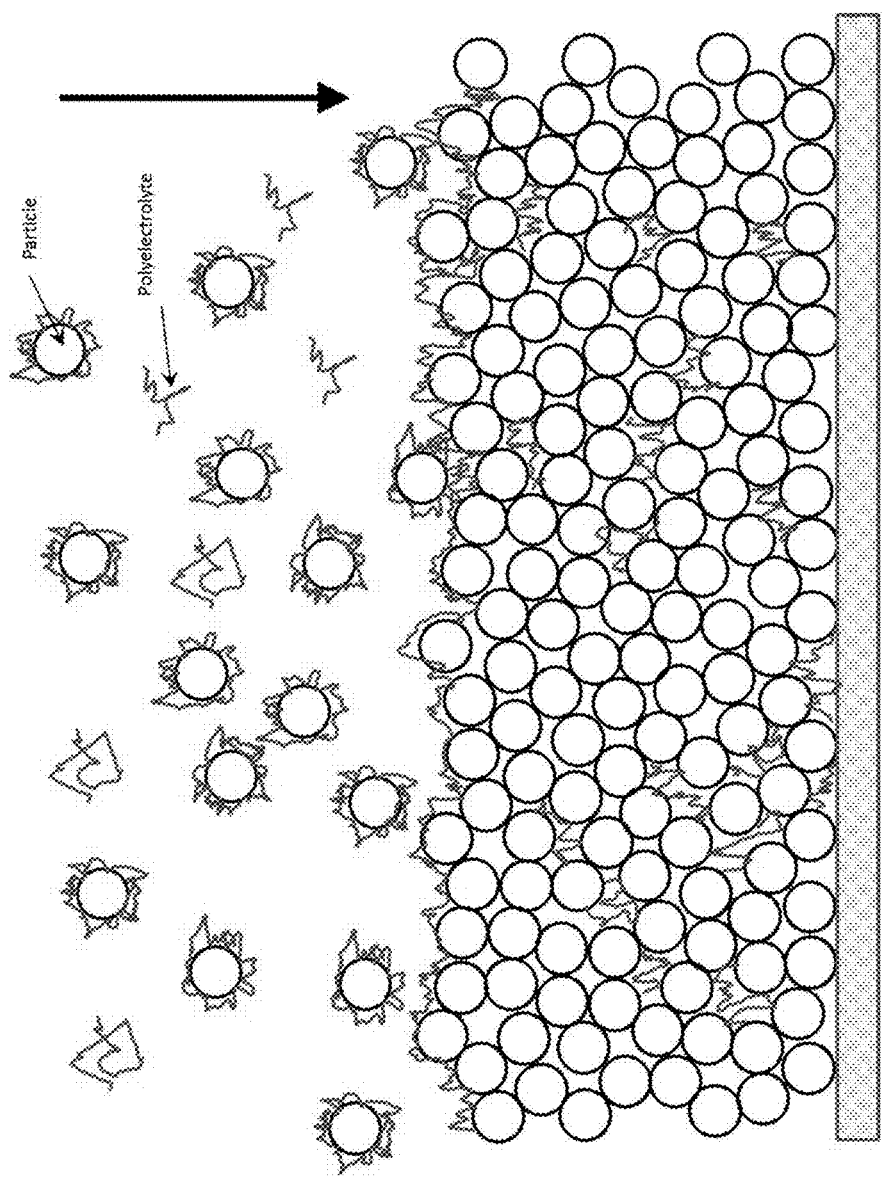
FIG. 5 is a schematic illustration of the sedimentation or filtration deposition process with a polyelectrolyte binder.
Figure 6:
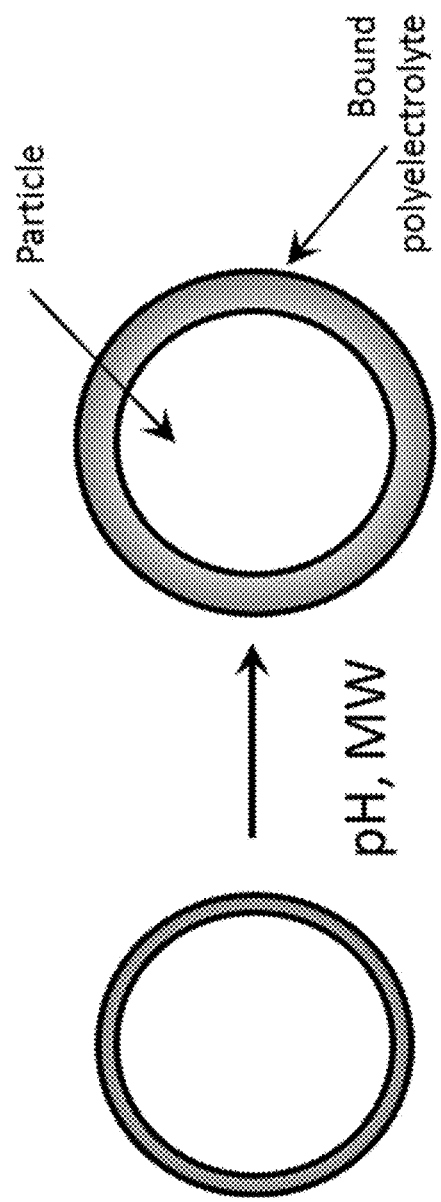
FIG. 6 is a schematic illustration of changes to the effective shell thickness.

Various techniques can be used to deposit the green layers of the porous media, i.e., to perform a layer-forming step of the method of the present invention. In one embodiment, particle layers can be formed by filtration or sedimentation of a dispersion of negatively charged spherical silica particles in an aqueous solution of a positively-charged polymer such as PDDA. Such a technique is useful for forming of a relatively thick layer of particles, and therefore is an efficient means of forming a filter cake for a substrate layer, or base layer, for the porous media. The polyelectrolyte acts to moderate the inter-particle forces as well as acting as a binder to temporarily consolidate the filter cake in its green state. Substrates formed in this manner with low molecular weight PDDA (e.g., 100,000-200,000 MW) can form porous media with a void fraction greater than 0.4, for example about 0.44. This mode of deposition is illustrated schematically in FIG. 5. Further, during such a deposition process, manipulating the pH of the dispersion can result in slight changes in void fraction within a range of about 0.04. While not being bound by theory, it is believed that changing the dispersion pH causes the swelling or contraction of the polymer, resulting in a change in the porous media void fraction. This phenomenon is illustrated schematically in FIG. 6.

Figure 7B:
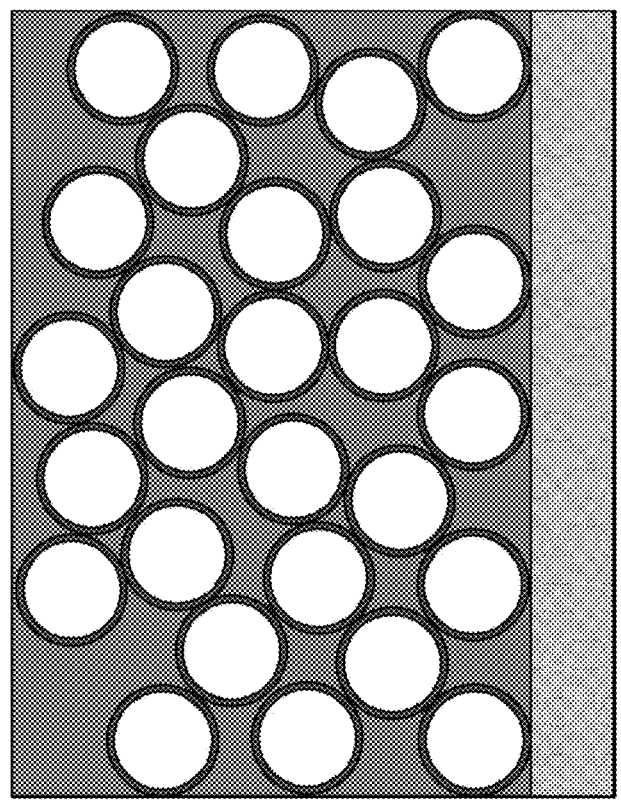
FIGS. 7A and 7B are a set of schematic illustrations of the sedimentation or filtration deposition process with a polyelectrolyte coating on the particles and a polyelectrolyte binder.
Figure 7A:
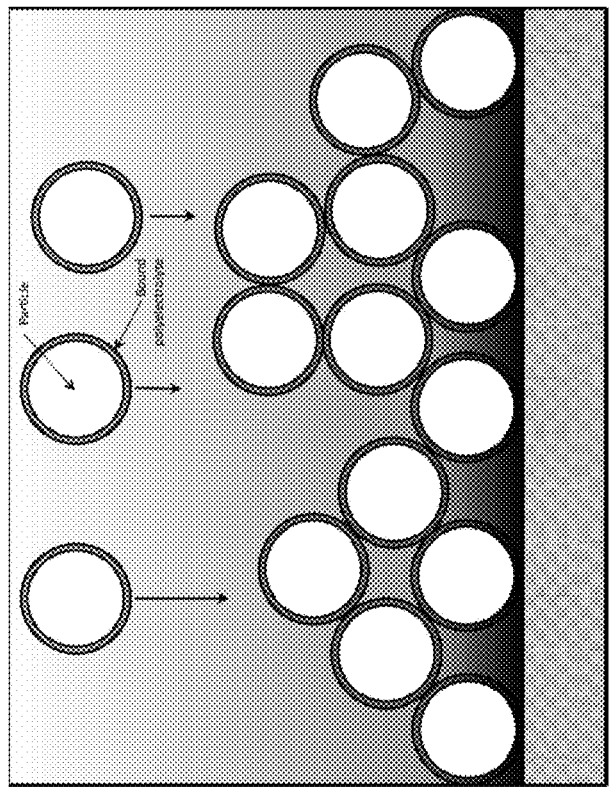

In various embodiments, control over the void fraction of the porous media is desirable to provide more flexibility for end-use applications. In one embodiment, an electrolytic polymer is first attached to the surface of the particles, and then the polymer-coated particles are dispersed in a solution or mixture comprising a dispersion polymer. In such an embodiment, the void fraction can be modified, as desired, by changing the characteristics of the polymer used for coating the particles while keeping the characteristics of the dispersion polymer relatively constant. The polymers used for coating and dispersing the particles, respectively, need not be of the same composition or molecular weight. For example, in a preferred embodiment, the low MW PDDA described above can be used as the dispersion polymer, while the resulting porous media void fraction can be manipulated by changing the characteristics of the coating polymer. Using relatively high MW polymers as the dispersion polymer can result in longer evacuation times, while lower MW dispersion polymers can decrease the mechanical strength of the filter cake in the green state. However, once an optimal MW for a given type of dispersion polymer is determined, it is contemplated herein that the void fraction of the porous media can be manipulated by changing the type and/or MW of the electrolytic polymer that is used to coat, or is otherwise attached to, the spherical particles. Notably, in such an embodiment, the choice of polymer used for coating has minimal effect on the evacuation time to draw down the initial dispersion. In one embodiment, the pH of the dispersion can also be manipulated to change the void fraction, as discussed above. The deposition method described herein is illustrated schematically in FIG. 7.

In another embodiment, a tape casting process can be used to perform the layer forming step of the method of the present invention. A solution comprising green core-shell particles and a binder can be used in such a tape casting process. One or more tape-casted layers can then be sintered to form the porous media composition of the present invention. An exemplary embodiment of a tape casting process can include the following steps. Particles are dispersed in a tape solution comprising one or more types of binder, polymer and/or polyelectrolyte. The solution is then cast or extruded into a tape, typically of a thickness on the order of 1 mm. The formulation is generally designed such that the tape remains flexible when dry. The dried tape can then be cut and shaped. Multiple thicknesses of the green tape may be stacked or laminated together to form a thicker implement than possible with a single layer of tape. In the case of a stacked or laminated implement formed from multiple layers of tape, an adhesive layer can be applied between the layers of tape. In one embodiment, the adhesive layer can comprise a slurry of particles and a binder. In another embodiment, the adhesive layer can comprise a diluted slurry of the particles dispersed in the tape solution, such that the adhesive layer has a composition similar to the tape itself. In yet another embodiment, the adhesive layer can be any type of adhesive material known in the art. In one embodiment, adjacent tape layers can comprise particles that are significantly different in size. Accordingly, the adhesive layer can comprise particles that are substantially similar in size to the particles of either of the two adjacent layers.

In one embodiment of the method of the present invention, the tape comprises core-shell particles in a matrix of polymer binders, plasticizers, or other additives. The tape is cast from slurry of core shell particles in an organic solvent including the aforementioned binder and plasticizer additives. The composition of the slurry is flexible, and those skilled in the art will be familiar with its formulation. In some embodiments, the slurry can include: Menhaden fish oil (Z-3), xylenes, ethanol, butyl benzyl phthalate, polyalkylene glycol, polyvinyl butyral (Butvar B-98) and cyclohexanone, as well as a dried powder of core/shell silica particles. The core-shell particles can be prepared as described previously herein.

Figure 12:
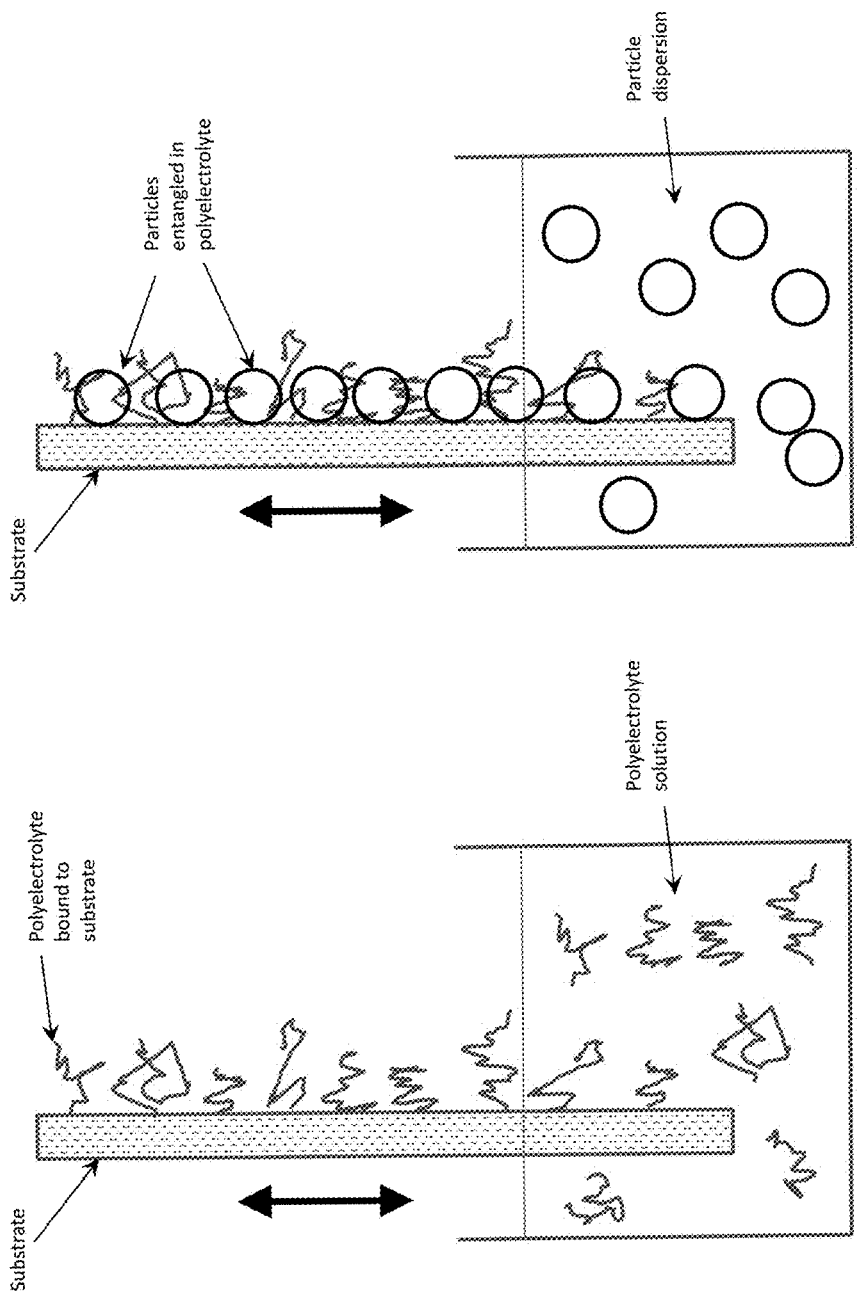
FIG. 12 is a schematic illustration showing the formation of the first layer of a layer-by-layer dip coating process.

In yet another embodiment, the layer forming step can be performed using a dip coating process. In dip coating, a film is built up by multiple sequential depositions of polyelectrolyte and spherical particles, as illustrated in FIG. 12. A substrate is first exposed to a polyelectrolyte solution, which binds to the substrate surface. The substrate is then typically rinsed, to remove excess unbound polyelectrolyte, then exposed to a mixture comprising spherical particles. The spherical particles become entangled in the bound polymer. The process can then be repeated to build a film of the desired thickness. This method effectively builds a shell-like coating on a substrate, similarly to the shell coatings that can be constructed on the outer surface of particles, as discussed previously. The substrate can comprise, for example, a silica film or silica-based glass, a silicon wafer (e.g., the film may be thermally grown or deposited from a tetraethylorthosilicate [TEOS] precursor), a glass frit, or a sheet of sintered spherical silica particles. However, the substrate material is not meant to be limited to any material specified herein and can be any material as would be understood by a person skilled in the art.

In one embodiment, the substrate is first hydroxylated and then immersed in a polyelectrolyte solution, for example a 12% solution of PDDA. The substrate is then rinsed with water and exposed to a dispersion of spherical silica particles. The mean size of the particles can vary over a wide range, depending on the desired porosity and properties of the resultant deposited film, and may range from 9 nm to 10 µm, as previously described herein. The substrate is them rinsed again with water. This coating sequence may be repeated as necessary to build the desired thickness of the final film on the substrate. The duration of the immersion and rinse steps maybe varied, but typically the duration of immersion would range from a few seconds to a few minutes. The deposited polymer/particle film and substrate may then be sintered to consolidate the structure as discussed previously.

In some embodiments, additives can be used to optimize the layer forming process. The layer forming step of the method of the present invention generally involves forming a layer of substantially spherical particles from a dispersion of such particles in a solvent, wherein the dispersion typically includes a polyelectrolyte that has been attached to the particles. In various embodiments, binders, plasticizers, or other additives can also be used in the dispersion. Binders such as poly(styrene sulfonic acid) or poly(ethylene oxide) can be utilized in the dispersion to form a more consolidated green part. The molecular weight of these substances can be adjusted to optimize the properties of the dispersion as well as the properties of the resulting porous media. Water soluble binders include, but are not limited to: poly(styrene sulfonic acid), poly(ethylene oxide), poly vinyl acetate-acrylic co-polymer, poly(vinyl alcohol), polyvinylpyrrolidone, poly(acrylic acid), poly(methylacrylic acid), polyacrylamide, polyethylenimine. Other water soluble binders include cellulose compounds, such as methylcellulose, hydroxypropylmethylcellulose, hydroxyethylcellulose, sodium carboxymethylcellulose, starches, dextrins, and alginates. Binders soluble in organic solvents include, but are not limited to: vinyls such as Poly(vinyl butyral) and poly(vinyl formal), and acrylics such as poly(methyl methacrylate). In addition, plasticizers, such as poly(ethylene glycol) can be added to the dispersion to impart mechanical flexibility, i.e., to make the green part and/or the resulting porous media more flexible. Plasticizers useful in the method of the present invention can include, but are not limited to: glycols, such as ethylene glycol, diethylene glycol, triethylene glycol and tetraethylene glycol; glycerols; and phthalates.

Once the layer or layers of the porous media is prepared, a sintering step is used in the method of the present invention to form a cohesive layer of spherical particles. In one embodiment, the green layer can be rinsed, for example with DI water or a solvent to remove undesired residues prior to sintering. Sintering is a process by which a powder is consolidated by heating to below the melting point. Particulate materials tend to consolidate due to the driving force for a reduction in surface free energy and thus surface area. Physically, this results in bridging between adjacent particles at points of contact, densification of the material, and a resulting reduction in porosity. While sintering can be used to control the degree of porosity in the method of the present invention, the primary purpose for sintering the porous media of the present invention is to yield robust mechanical bonds between adjacent particles, resulting in a self-supporting, cohesive structure. As the sintering process is driven by a reduction in surface energy, smaller particles of equivalent composition tend to sinter at lower temperatures. Accordingly, when processes of the present invention are used to produce multi-layer porous media having layers comprising differently-sized particles in each layer, the largest particles generally must be deposited and sintered first. This is due to the need to sinter the larger particles at higher temperatures than smaller particles. After the layer with the largest particle is sintered, a layer of smaller particles can be deposited on the largest layer and then sintered at a lower temperature. Layers of progressively smaller particles can then be built up and sintered at progressively lower temperatures so that the structure of the earlier deposited layers is not disturbed.

Figure 9B:
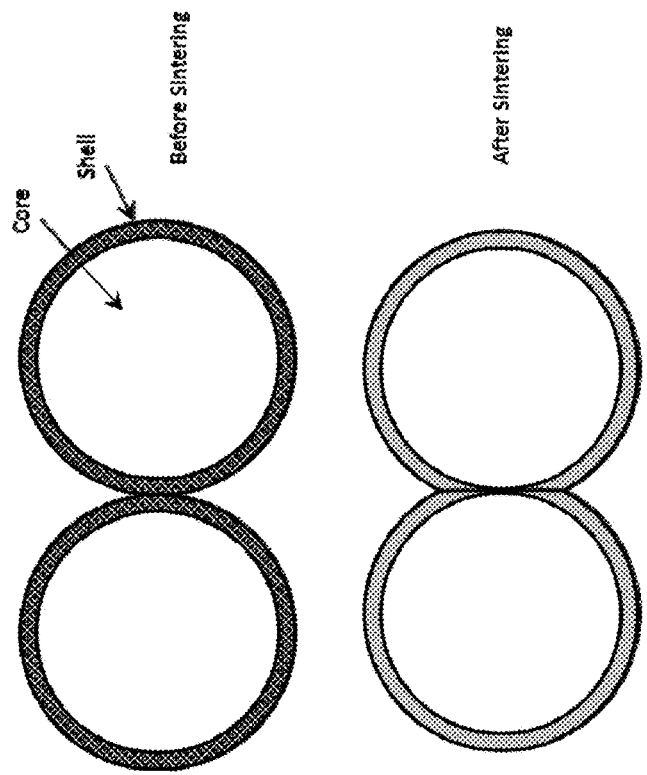
FIGS. 9A and 9B are a set of schematic illustrations showing a sintering process without a shell layer (FIG. 9A) and with a shell layer (FIG. 9B).
Figure 9A:
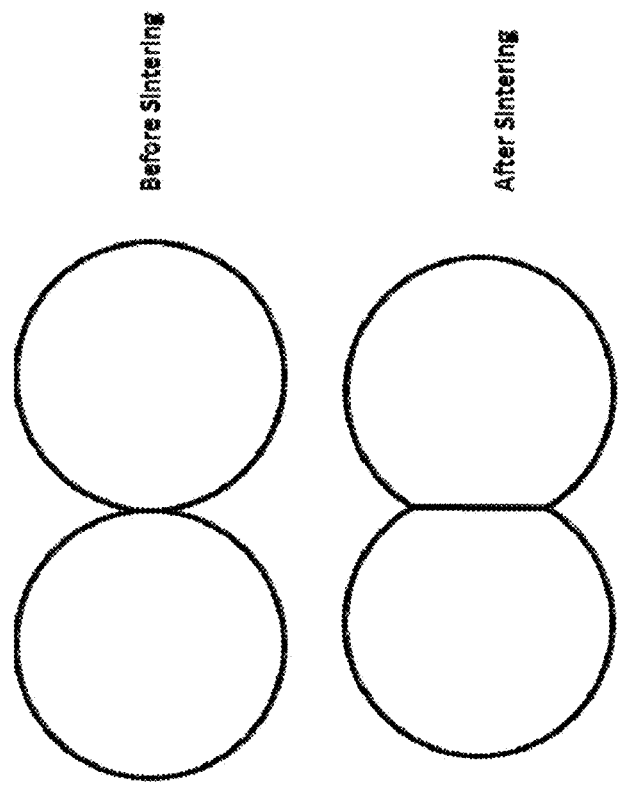

In one embodiment, the core-shell coating approach described previously herein can be used to allow for a lower-temperature sintering process than otherwise achievable. The shell coating is formed from sol particles that are much smaller than the core particles, for example, in one embodiment, sol particles of about 9 nm in diameter can be used with core particles 1700 nm in diameter. Accordingly, the smaller sol particles will sinter at much lower temperatures than the core, forming a hard cohesive shell around the core and also a cohesive bond between adjacent core-shell particles. In this manner a cohesive structure is formed. The sintering process with and without a shell layer is illustrated schematically in FIG. 9. FIG. 9A shows particles without a shell before and after sintering, while FIG. 9B shows core-shell particles before and after sintering. The core-shell approach can also be used to sinter spherical core particles of differing size at similar temperatures, whereas if the shell layer was not present, large diameter particles would require dramatically higher temperatures than smaller diameter particles. As previously described herein, the shell particles of the individual core-shell particles can be at least partially sintered to each other, i.e., the shell is at least partially consolidated, prior to sintering a plurality of core-shell particles together to form the porous media of the present invention.

In various embodiments, the sintering step of the present invention can be performed at any suitable temperature and for any desired duration. In one embodiment, the sintering step can be performed at any temperature in the range 100 to 1200° C. However, the temperature of the sintering step or steps is not meant to be limited by any specific temperature cited herein and can be any temperature, as would be understood by a person skilled in the art. Accordingly, the temperature and duration of the sintering step can be modified depending on the composition of the particles used to form the porous media of the present invention, and depending on the desired porosity or consolidation of the porous media to be formed. In various embodiments, the sintering step can include a "burn-out" phase wherein the polymers or other additives associated with the particles, e.g., core-shell particles are degraded, volatilized, or otherwise modified via heating. In one embodiment, the burn-out phase can be performed at a significantly lower temperature than other portions of the sintering step.

Once the first layer, or substrate layer, is consolidated by sintering, subsequent layers may be deposited by one of the layer forming techniques described herein and sintered. In one embodiment, each subsequent layer comprises particles that are at least less than about half the diameter of the particles of the previous layer, and at least greater than about 0.15 times the diameter of the particles of the previous layer, i.e., the layer upon which the new particles are being deposited. This sizing sequence prevents the particles of the new layer from penetrating substantially into the interior of the layer upon which they are being deposited. Accordingly, each subsequent particle layer will be a relatively discrete layer. In various embodiments, each subsequent layer can be connected to the previous layer via sintering, i.e., at least a portion of the particles at the interface between two layers are sintered together.

The thickness of each subsequent layer can be varied, as would be understood by a person skilled in the art. For example, in one embodiment, each subsequent layer can be significantly thinner than the base or substrate layer, thereby reducing fluid flow limitations associated with the lower throughput imposed by relatively low void fraction layers. In one embodiment, each subsequent layer can be thinner than the previous layer. In one embodiment, all of the layers can have substantially the same thickness.

In another embodiment, when the green part is formed by tape casting, the tape cast film may be as thick as possible, but is typically on the order of 2 mm thick or less. Thicker layers of a given particle size can be formed by stacking multiple layers. In one embodiment, an adhesive layer comprising a slurry of core-shell particles can be used to make the tape layers stick together in the green state. This adhesive layer can be comprised of a slurry of the tape in a solvent, for example ethanol, and optionally a binder, such as Butvar B-98. An adhesive layer can serve to not only bind the layers together in the green state, but provides a source of inter-layer particles which may infuse in the surfaces of the adjacent layers to enable more effective sintering of the adjacent layers.

Figure 11:
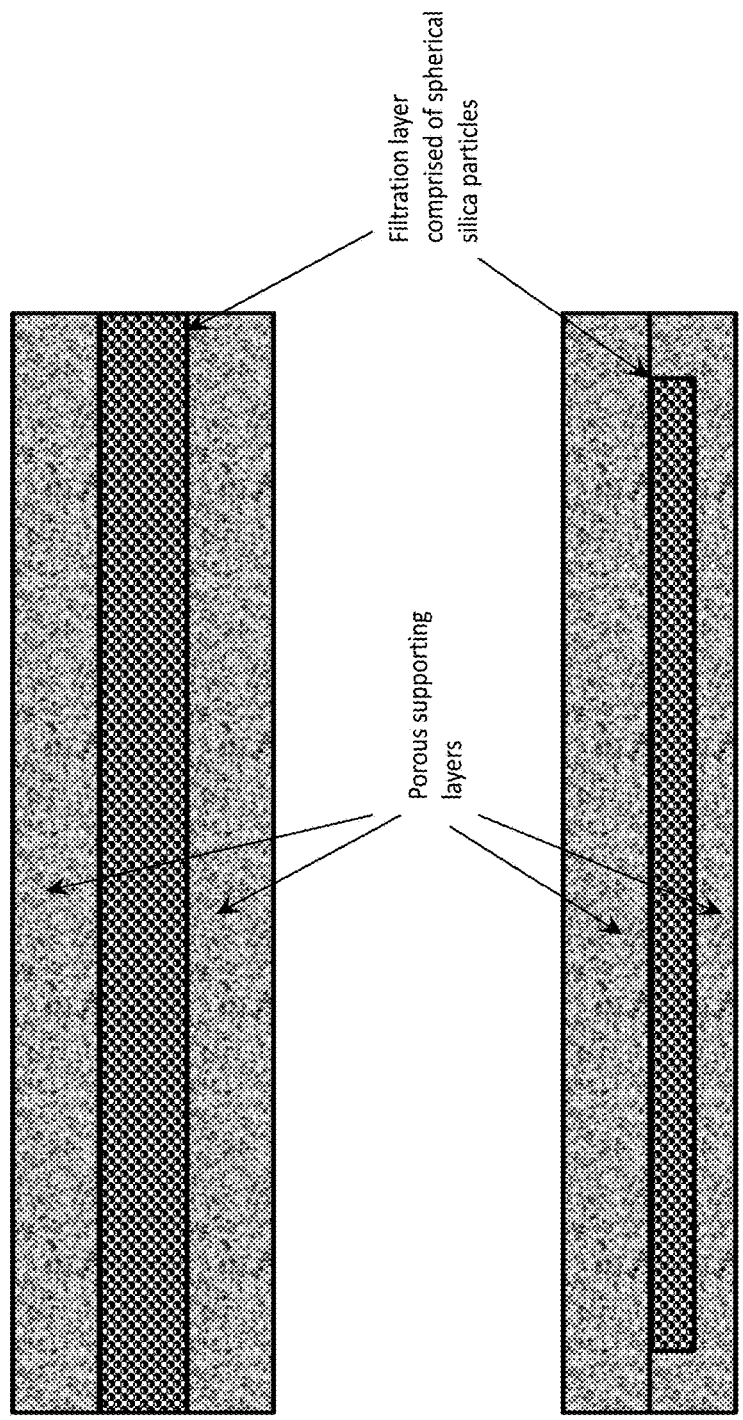
FIG. 11 is a schematic illustration of an exemplary embodiment of a filter media of the present invention having a filtration layer, comprised of spherical silica particles, sandwiched between two porous layers.

In various embodiments, the porous material of the present invention can be used in conjunction with a substrate or another type of filtration media. For example, as shown in FIG. 11, a sheet of the porous media of the present invention can be laminated between substantially more porous layers. In one embodiment, the adjacent layers can comprise a glass frit. In this manner, the adjacent layers provide physical support for the porous media and minimal restriction to flow, while utilizing a minimum of spherical silica particles.

Figure 15B:
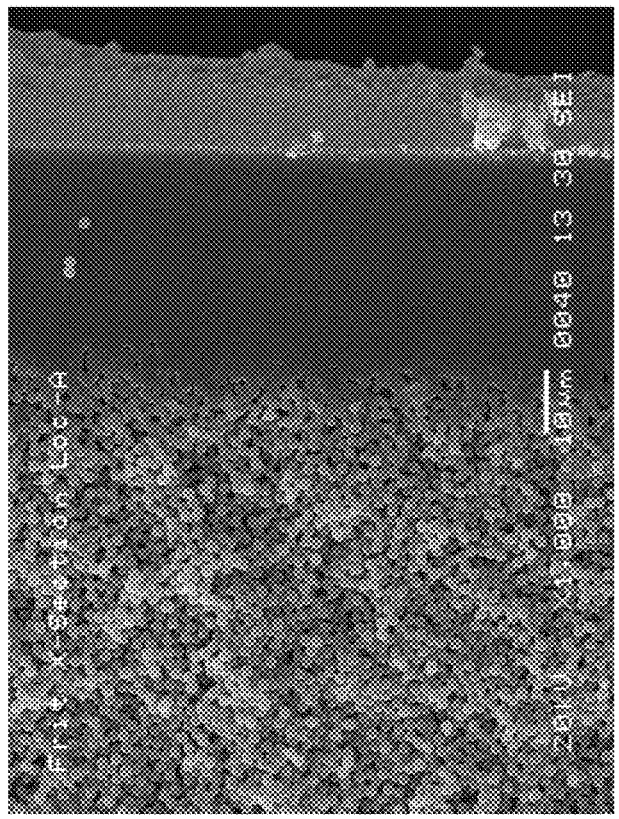
FIG. 15B is a high magnification electron micrograph of an exemplary embodiment of the porous media of the present invention fabricated by tape casting, showing the edge region where the sides of the piece of media have been substantially sealed or fused by a laser.
Figure 15A:
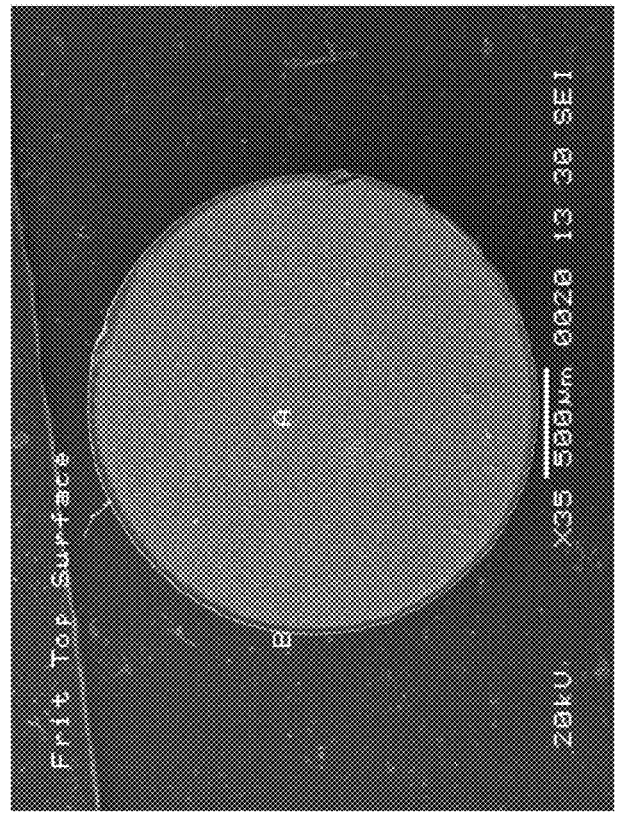
FIG. 15A is a low magnification electron micrograph of an exemplary embodiment of the porous media of the present invention fabricated by tape casting, showing the edge region where the sides of the piece of media have been substantially sealed or fused by a laser.

In various embodiments, the porous media or composite porous media of the present invention can be made into any shape, as would be understood by a person skilled in the art. In one embodiment, a large sheet of porous media can be fabricated, such as by tape casting. Smaller pieces of a desired shape, for example a circle or rectangle, can be cut from the sheet to be used in an application, as needed. For example, in one embodiment, the smaller pieces can be cut from the larger sheet using a laser, water jet, or any other suitable cutting technique. In one embodiment, when a laser is used to cut a fragment or piece of sintered porous media of the present invention, it is contemplated herein that the edges or sides of the piece of media can be substantially sealed by the laser as shown in FIG. 15. Accordingly, in such an embodiment, the porosity of the media through the cross-section, i.e., side of the piece, can be significantly less than the porosity through the portions of the piece that were not contacted by the laser. In addition, the portion of the piece of media exposed to the laser can form a glassy layer that can strengthen the otherwise potentially friable edges of the piece. In other embodiments, at least a portion of a piece of sintered porous media can be sealed via other methods, such as by coating a portion of the media with a polymer.

In another embodiment, a piece of porous media can be fabricated into the desired shape via a molding technique. In such an embodiment, the layering and sintering process as described above can be performed with a mold, so that the resulting porous media is formed into the shape of the mold. Various techniques known to those skilled in the art may be employed such as slip casting, gel casting, and injection molding.

In various embodiments, the sintered porous media of the present invention can be used in any application having a need for a porous media, for example, but not limited to: an end frit for a chromatography column, or in any other apparatus requiring a frit or filter; and any apparatus used for solid phase extraction. In one embodiment, the surface of the porous media can be functionalized with an octadecyl carbon chain ($C_{18}$), an octyl carbon chain ($C_8$), a phenyl group, a cyano group or other functional group. The methods and chemistry required to achieve these types of surface functionalizations are well known to those skilled in the art.

Figure 16:
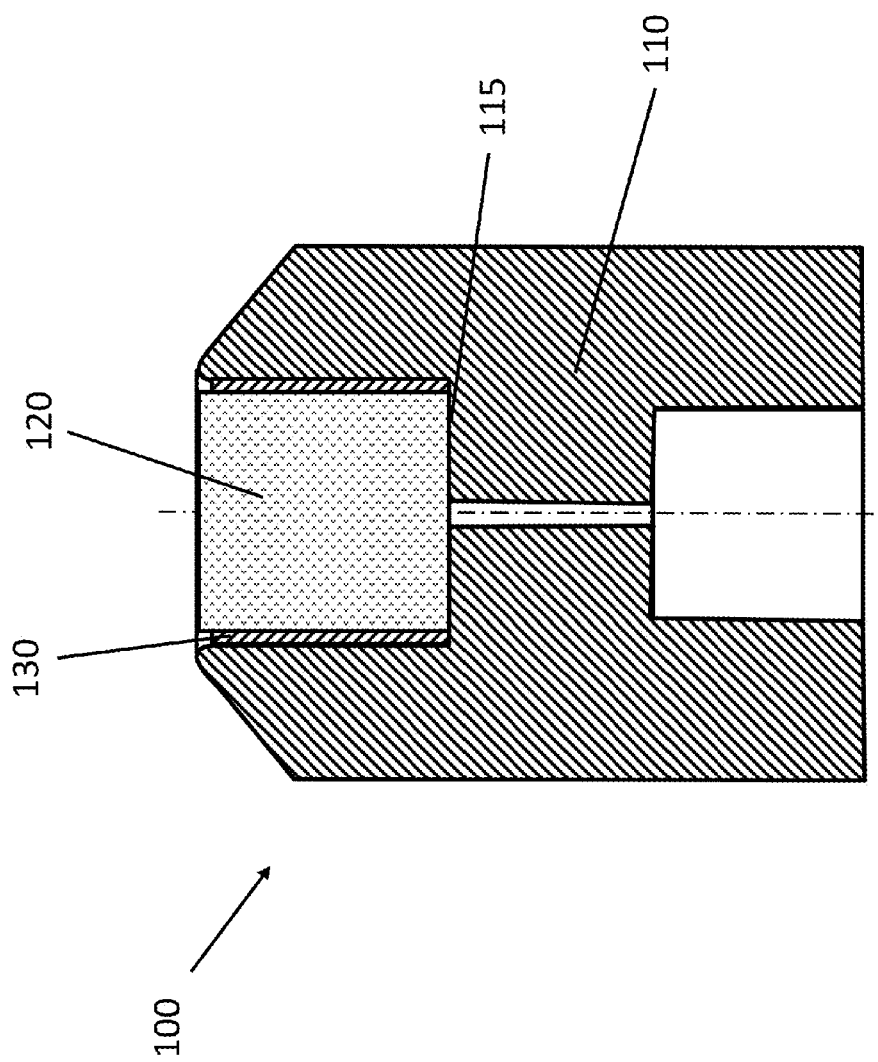
FIG. 16 is a schematic diagram showing an exemplary embodiment of a frit holder for a chromatography column. In the embodiment shown, the frit is encased in a polymeric sealing sleeve and inserted into the frit holder.

In one embodiment, a cylinder of the porous media can be included in a polymeric sleeve and inserted into a chromatography column having a frit holder. For example, referring now to FIG. 16, an exemplary frit holder 100 is shown. Frit holder 100 includes a housing 110 having a receiving section 115. In one embodiment, a cylindrical piece of porous media 120 is inserted into a polymeric sleeve 130. The sleeve-encased porous media 120 is then inserted into receiving section 115 of frit holder 100, such that the edges around the frit are suitably sealed while leaving the remaining portions of the frit suitably porous to allow fluid to flow through the frit and into a column that is connected to frit holder 100.

In one embodiment, the sleeve can be fabricated from appropriately-sized plastic tubing, for example polytetrafluoroethylene tubing. The frit 120 and sleeve 130 can be sized to have partial interference when inserted into the frit holder, such that a positive seal is obtained via a friction fit. In one such embodiment, the inner diameter of receiving section 115 of frit holder 100 is 0.093 inches and the outer diameter of the combined frit and sleeve is 0.094 inches. This embodiment is preferred in that it provides for a positive seal around the edges of the frit, while minimizing stress on the potentially brittle porous media cylinder. However, the dimensions of the frit and/or sleeve are not limited to any specific dimensions described herein, and can be sized for any column or other frit application, as would be understood by a person having ordinary skill in the art. In addition, the shape of the frit is not limited to any specific shape described herein and can be a shape other than a cylinder.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1

Filter Media Comprising Sintered Core-Shell Particles

Core-shell particles are prepared as follows. Densified, substantially monodisperse and spherical 1.7 µm particles are prepared with a polymer/sol shell coat. Depending on the size range of interest, different processes can be used to synthesize the primary, i.e., core, particles. For particle sizes up to about 1 µm in diameter, an effectively monodisperse, silica sol can be prepared using the Stöber method [Stö,ber et al, 1966, J. Colloid Interface Sci., 26: 62]. For larger particles, a modification of a method described by Unger et al can be used [Unger et al., 1988 U.S. Pat. No. 4,775,520]. Densification of 1.7 µm core particles is achieved by sintering at 1000° C. for 26 hours. Also note that particles fabricated via other methods can be substituted, provided they meet the size and shape requirements.

The 1.7 µm particles were first hydroxylated by exposing them to a 2% solution of hydrofluoric acid at a temperature of approximately 100° C. for 24 hours. The particles were then washed, by multiple steps of dilution with water and centrifugation to concentrate the particles. The washed particles were then boiled in pure deionized water for 24 hours to remove the residual acid. The particles were then washed again, by multiple steps of dilution with water and centrifugation to concentrate the particles. The particles were then exposed to a 12% by weight solution of PDDA, and again washed through dilution with water and centrifugation. The polymer coated particles were then exposed to a 2% solution of 9 nm silica sol and again washed through dilution with water and centrifugation. The PDDA exposure/sol exposure cycle can be repeated until the desired coating thickness is achieved. In this example, 4 coats were applied. This core/shell particle was then dried and served as the powder that was introduced into the tape casting slurry.

Figure 13B:
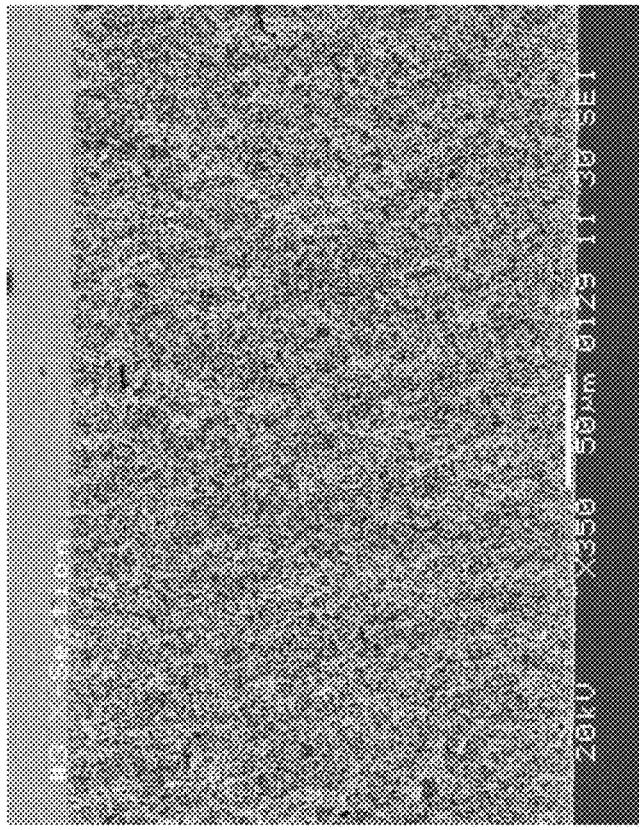
FIGS. 13A and 13B are a set of scanning electron micrographs.
Figure 13A:
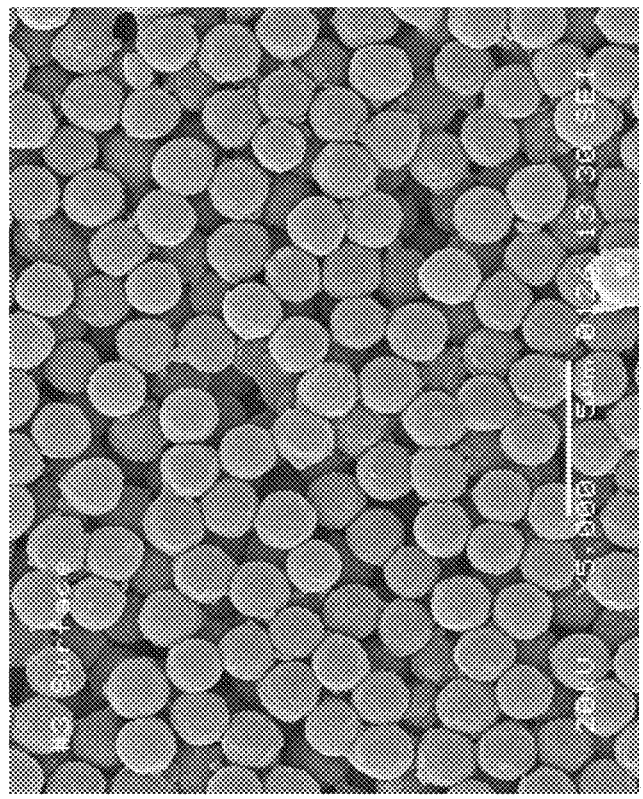
Figure 14:
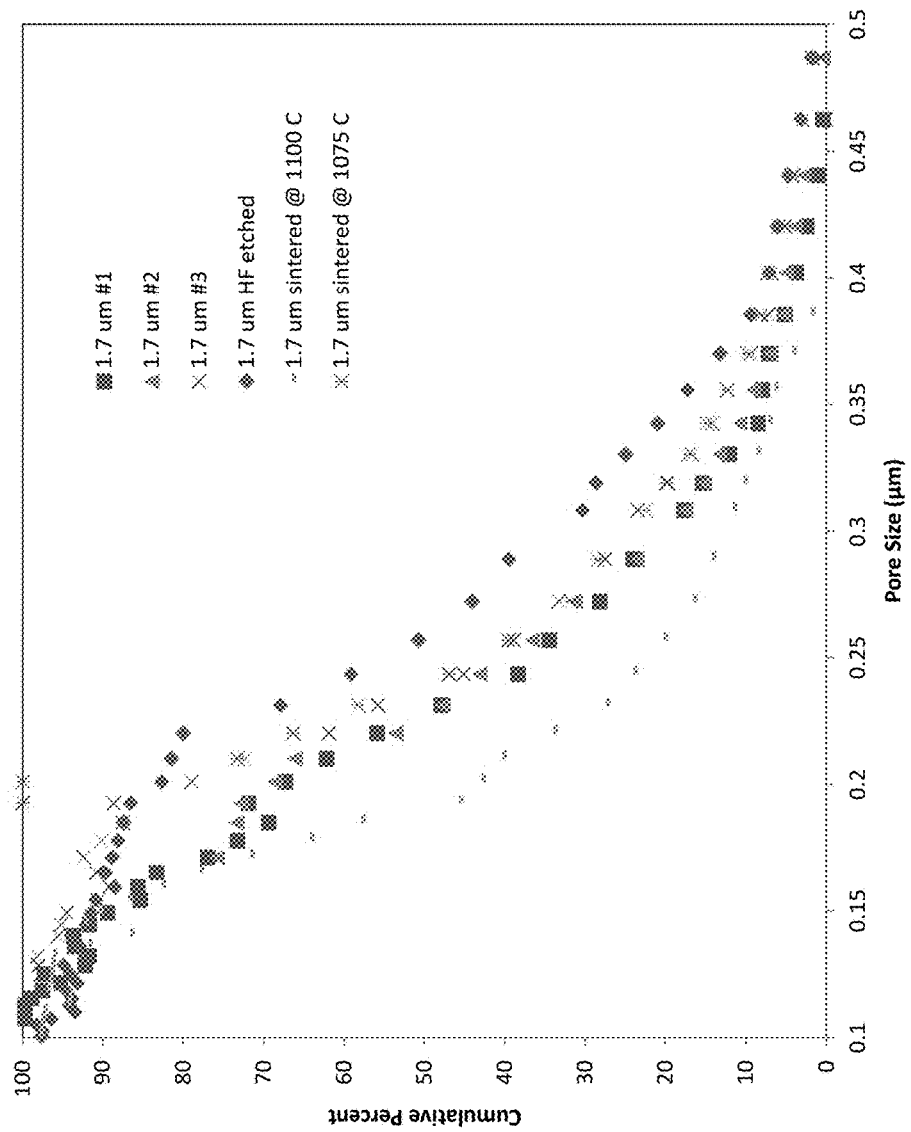
FIG. 14 is a graph showing the pore distribution of various embodiments of the porous media of the present invention fabricated by tape casting.

The tape casting process is well known to those skilled in the art. A review of the process is provided in Rahaman (Rahaman, 2003, Ceramic Processing and Sintering, $2^{nd}$ edition, CRC press). Multiple layers of the tape can be stacked or laminated in order to fabricate a thicker material. It can be efficacious to provide a "glue layer," i.e. an adhesive layer, between the individual sheets of tape in order to bind them together in the green state, as well as to provide a source of inter-layer particles to enable the layers to be more effectively sintered together. A slurry of equal parts by weight of the green tape and ethanol with 5% by weight of Butvar B-98 was introduced on the surface of one of the layers in a thin film. The film can be applied by a paint brush or any other suitable method. The second layer was then pressed onto the first layer, forming a consolidated green laminate. The layer or layers can then be sintered to form a free standing porous media. Before sintering, the parts can be heated under vacuum to about 80° C. for about 12 hours to drive off any excess solvent in order to prevent spalling or delamination of the layer during sintering. The green part can be consolidated by sintering at a temperature between about 1050 and 1100° C. for about 24 hours. It is advantageous to include a "burn-out" phase in the temperature profile of the sintering cycle, including 4 hour soaks at 325 and 580° C., respectively. Porous media fabricated by this method exhibit a morphology as illustrated in FIG. 13, and a pore distribution as illustrated in FIG. 14. Nitrogen permeability data collected on these porous media indicate a void fraction in the range of 0.4-0.5, depending on the core particle size and the sintering conditions, and most typically between about 0.45 and 0.5.

Example 2

Filter Media Via Sedimentation

Figure 10:
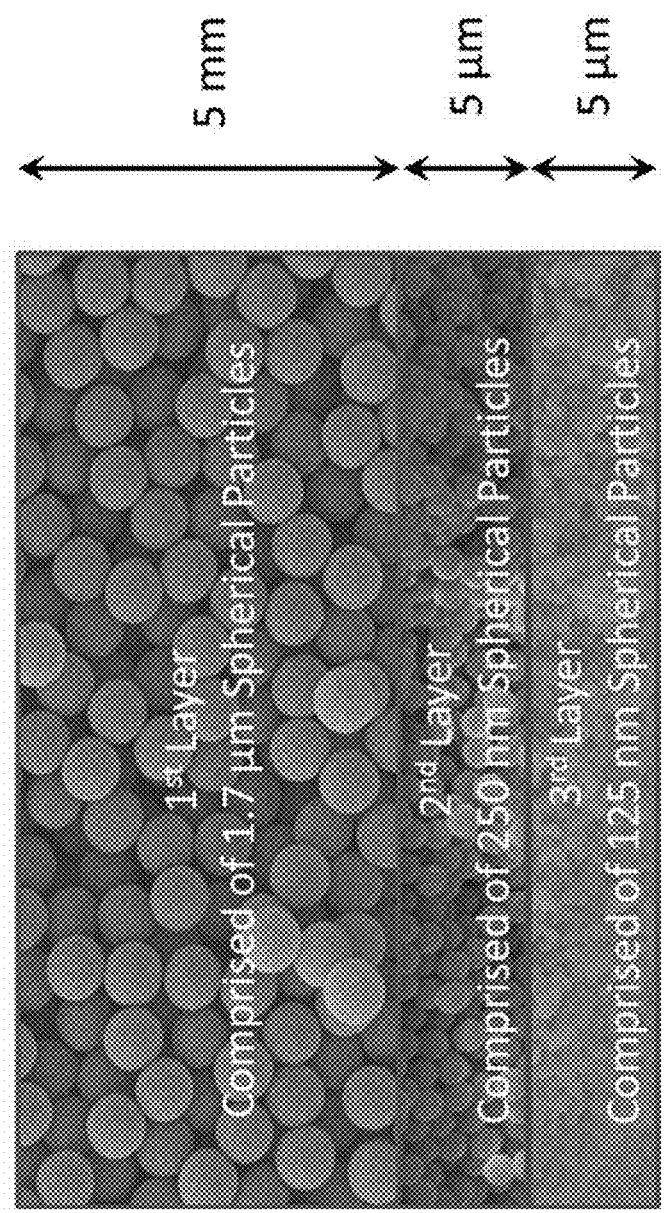
FIG. 10 is a schematic illustration of an exemplary embodiment of the composite porous media of the present invention comprising a filter media composed of three layers.

A multiple-layer filter media was produced via a sedimentation method. The filter media comprises a first layer of particles that were deposited by a filtration or sedimentation method, as shown in FIG. 10. This first layer can be composed of s comparatively thick layer of relatively large particles, that when sintered, forms a rigid and robust mass for the deposition of subsequent layers. In this example, this first layer comprises a 3 to 5 mm thickness of 1.7 µm spherical silica particles and has void fraction in the range of 0.4-0.6. The range of particle sizes employed in this first layer can vary, and while not intending to be limited by the sizes described herein, a preferred range of sizes is between about 1 and 5 µm. A second layer is intimately bonded to the first layer, the second layer comprising a 5 µm thickness of 250 nm spherical silica particles with void fraction in the range of 0.26-0.6. A third layer is intimately bonded to the second layer, such that the second layer is between the first and third layers, this third layer comprising a 5 µm thickness of 125 nm spherical silica particles with a void fraction in the range of 0.26-0.6.

This example yields a filter media with a theoretical absolute solids retention on the order of about 10 nm, while also providing an "integrated pre-filter," i.e. the first layer, with a reasonably high capacity and retention on the order of 0.25 µm. Based on the model illustrated in FIG. 3, and assuming a void fraction of 0.55 for all layers, the structure shown in FIG. 10 can allow a throughput (linear velocity) of about 650 µm/s of water at ambient conditions and a differential pressure of 2 atm.

The porous media was fabricated according to the following method. 1.7 µm particles were prepared with a polymer/sol shell coat. The 1.7 µm particles were first hydroxylated by exposing them to a 2% solution of Hydrofluoric acid at a temperature of approximately 100° C. for 24 hours. The particles were then washed, by multiple steps of dilution with water and centrifugation to concentrate the particles. The washed particles were then boiled in pure deionized water for 24 hours to remove the residual acid. The particles were then washed again, by multiple steps of dilution with water and centrifugation to concentrate the particles. The particles were then exposed to a 12% by weight solution of PDDA, and again washed through dilution with water and centrifugation. The polymer-coated particles were then exposed to a 2% solution of 9 nm silica sol and again washed through dilution with water and centrifugation.

Approximately 4 g of the shell coated particles were then dispersed in a 5% by weight solution of PDDA of total volume 40 ml. The pH of this dispersion was adjusted to a target value typically in the range of 4-6, and most preferably around 5. This dispersion was filtered into a cake. The cake was then washed with an excess of deionized water, typically at least 50 ml. The cake was removed from the filter while still damp, air dried for at least 4 hours then dried in a vacuum oven for at least 12 hours. The dried cake was then sintered at a temperature around 1140° C. for about 12 hours. This sintered element was then fixtured into a housing. A dispersion of about 10 mg of 250 nm particles in a 5% by weight solution of PDDA of total volume 40 ml was prepared. The pH of this dispersion was adjusted to a target value typically in the range of 4-6, and most preferably around 5. This dispersion was then filtered through the substrate fixtured in the housing, such that the 250 nm particles, combined with the PDDA binder, formed a thin layer on the surface of the substrate. This layer was then washed with an excess of water, typically at least 50 ml. This multilayered media was removed from the housing and sintered at a temperature of around 1050° C. Subsequent layers can be deposited by a similar procedure using the appropriate amounts of material to achieve the desired layer thickness and sintered at the appropriate temperature. Typically material is deposited such that each additional layer can be sintered at a subsequently lower temperature, such that the sintering of subsequent layers does not significantly affect the structure of previously deposited and sintered layers.

Example 3

Chromatography Columns Utilizing Frits Comprised of Novel Porous Media

Chromatography columns were produced using fits comprised of the novel porous media and compared to columns using conventional stainless steel frits in a controlled experiment. These novel porous media frits were functionalized with a $C_{18}$ group, to match the surface chemistry of the packing media in the column, utilizing chemistry and methods well known to those skilled in the art. In a typical chromatography column, porous frits are utilized to contain the particulate column packing media in the column. The frit should be designed to withhold the column packing media, while presenting minimal resistance to flow and also causing minimal loss of separation efficiency. However, fits can be a component of efficiency degradation in chromatographic separations through a phenomenon known as band broadening. Further, conventional fits have been shown to be compromised in their ability to withhold particles with nominal diameters below about 2.0 µm.

A total of 20 chromatography columns were loaded in 5 separate trials, with each trial consisting of 4 columns being loaded via the same method. One trial consisted of 4 columns utilizing only conventional stainless steel frits. For the remaining 4 trials, each included one control column utilizing only conventional stainless steel frits. Two of these trials included 2 columns with a porous media frit as described in the present disclosure, wherein the porous media frit was included only at the column outlet, and a conventional stainless steel frit was included at the column inlet. Further, these two trials included 1 column with porous media fits at both the column inlet and column outlet. The two remaining trials contained 1 column with a porous media frit only at the column outlet and a conventional stainless steel frit at the column inlet, and 2 columns with porous media frits at both the column inlet and column outlet. Multiple chromatographic separations were performed on each column using a set of reference compounds.

Multiple metrics can be used to characterize chromatographic performance, and parameters such as a measure of separation efficiency (in this example the number of theoretical plates) and a measure of peak symmetry (in this example the tailing factor) are widely used. A detailed description and derivation of these parameters is included in multiple reference works (for example, Snyder, L. R.; Kirkland, J. J.; Dolan, J. W., *Introduction to Modern Liquid Chromatography*, $3^{rd}$ Edition, Wiley 2010 which is hereby incorporated by reference). For the present example, it is sufficient to note that a higher value for the number of theoretical plates exhibited by a chromatographic peak in a reference standard represents superior performance, and also that a peak asymmetry value closer to unity also represents superior performance.

Table 2 includes results of the experiment in terms of separation efficiency. Table 3 includes results of the experiment in terms of peak symmetry. In terms of both performance metrics, the set of columns having porous media frits on both inlet and outlet ends exhibited superior performance compared to the set of columns having conventional stainless steel frits. The improvement in efficiency is on the order of 6.5% and the porous media fits also resulted in a peak symmetry significantly closer to unity.

TABLE 2

Separation Efficiency

| Frit Type | # of Columns | # of injections | Plate Count | Standard Deviation |
|---|---|---|---|---|
| Stainless Steel | 8 | 20 | 9804 | 393 |
| Porous media frit (outlet only) | 6 | 18 | 10330 | 505 |
| Porous media frit (both ends) | 6 | 18 | 10446 | 294 |

TABLE 3

Peak Symmetry

| Frit Type | # of Columns | # of injections | Asymmetry Factor | Standard Deviation |
|---|---|---|---|---|
| Stainless Steel | 8 | 20 | 1.093 | 0.041 |
| Porous media frit (outlet only) | 6 | 18 | 1.083 | 0.047 |
| Porous media frit (both ends) | 6 | 18 | 1.015 | 0.025 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of making a porous material comprising:
    providing a plurality of substantially spherical core particles having a diameter of at least 1 micron,
    contacting the core particles with a polymer such that at least a portion of the surface of the core particles is coated with the polymer,
    forming a plurality of core-shell particles by contacting the polymer-coated core particles with a plurality of shell particles, wherein the plurality of shell particles are bound to the polymer coated core particles,
    drying the core-shell particles, and
    sintering together the contact point of the shells of adjacent core-shell particles to form bonds between the adjacent core-shell particles, thereby forming a bonded porous material.

2. The method of claim 1, further comprising one or more additional shell-forming steps, wherein each shell forming step comprises:
    contacting the core-shell particles with a polymer such that at least a portion of the surface of the core-shell particles is coated with polymer, and
    contacting the polymer-coated core-shell particles with a plurality of shell particles, wherein the plurality of shell particles are bound to the polymer coated core-shell particles.

3. The method of claim 1, further comprising the steps of suspending the dried core-shell particles in a binding solution to form a binding mixture, and extruding the binding mixture to form a tape comprising particles prior to sintering.

4. The method of claim 1, further comprising forming a sintered porous implement from the porous material and sealing an edge of the implement.

5. The method of claim 4, wherein the implement is formed by cutting the porous material with a laser.

6. The method of claim 4, further comprising the step of forming a cylindrical frit implement.

7. The method of claim 1, wherein the step of sintering the core-shell particles comprises the steps of:
    at least partially sintering the core-shell particles to form consolidated particles, and
    sintering the consolidated particles to form bonds between adjacent particles, thereby forming a bonded porous material.

8. The method of claim 1, wherein the shell particles are smaller than the core particles.

9. The method of claim 8, wherein the core particles comprise silica.

10. The method of claim 9, wherein the core-shell particles comprise a material selected from the group consisting of silica, titania, alumina, antimony oxide, zinc oxide, tin oxide and iron oxide.

11. A method of making a porous material comprising the steps of:
providing a plurality of substantially spherical core particles,
contacting the core particles with a polymer such that at least a portion of the surface of the core particles is coated with the polymer,
forming a plurality of core-shell particles by contacting the polymer-coated core particles with a plurality of shell particles, wherein the plurality of shell particles are bound to the polymer coated core particles,
drying the core-shell particles, and
sintering together the contact point of shells of adjacent core-shell particles to form bonds between the adjacent core-shell particles, thereby forming a bonded porous material wherein the degree of porosity of the bonded porous material is controlled by sintering.

12. The method of claim 11, wherein the core-shell particles are substantially spherical.

13. The method of claim 11, wherein the shell particles are smaller than the core particles.

14. The method of claim 13, wherein the step of contacting the core particles with a polymer such that at least a portion of the surface of the core particles is coated with the polymer comprises the step of:
coating the core with a polymer comprising a polyelectrolyte to form a polymer-coated core.

15. The method of claim 14, further comprising the step of contacting the core with an acid.

16. The method of claim 11, where the size of the core-shell particles is greater than about 1 micron.

17. The method of claim 11, where the void fraction of the porous material is greater than about 0.4.

18. The method of claim 11, where the relative standard deviation of the core-shell particle size is less than about 10 percent.

19. The method of claim 11, further comprising the steps of:
suspending the core-shell particles in a binding solution to form a binding mixture, and
extruding the binding mixture to form a tape comprising core-shell particles.

20. The method of claim 11, wherein the core-shell particles are in a green state prior to sintering to form the porous material.

21. The method of claim 11, further comprising the step of functionalizing the surface of the porous material.

22. A method of making a porous material comprising the steps of:
providing a plurality of core-shell particles having a solid core comprising silica and one or more shell layers;
wherein the one or more shell layers are selected so as to be sinterable at a lower temperature than the core, the one or more shell layers comprise shell particles smaller than the core particles to provide the lower sinterable temperature of the one or more shell layers; and
sintering together the contact point of shells of adjacent core-shell particles to form bonds between the adjacent core-shell particles, thereby forming a bonded porous material.

23. The method of claim 22, wherein the core-shell particles comprise a material selected from the group consisting of silica, titania, alumina, antimony oxide, zinc oxide, tin oxide and iron oxide.

24. The method of claim 23, wherein the shell layers comprise silica.

* * * * *